(12) United States Patent
Seguin et al.

(10) Patent No.: US 7,892,281 B2
(45) Date of Patent: *Feb. 22, 2011

(54) PROSTHETIC VALVE FOR TRANSLUMINAL DELIVERY

(75) Inventors: Jacques Seguin, Old Windsor (GB); Georg Börtlein, Meudon (FR)

(73) Assignee: Medtronic CoreValve LLC, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/348,892

(22) Filed: Jan. 5, 2009

(65) Prior Publication Data

US 2009/0164006 A1 Jun. 25, 2009

Related U.S. Application Data

(63) Continuation of application No. 12/029,031, filed on Feb. 11, 2008, which is a continuation of application No. 11/352,614, filed on Feb. 13, 2006, now Pat. No. 7,329,278, which is a continuation of application No. 10/412,634, filed on Apr. 10, 2003, now Pat. No. 7,018,406, which is a continuation-in-part of application No. 10/130,355, filed as application No. PCT/FR00/03176 on Nov. 15, 2000, now Pat. No. 6,830,584, and a continuation-in-part of application No. PCT/FR01/03258, filed on Oct. 19, 2001, application No. 12/348,892, which is a continuation of application No. 11/434,506, filed on May 15, 2006, which is a continuation-in-part of application No. 10/772,101, filed on Feb. 4, 2004, which is a continuation-in-part of application No. 10/412,634.

(30) Foreign Application Priority Data

Nov. 17, 1999 (FR) .................................. 99/14462
Nov. 17, 1999 (FR) .................................. 99/14462

(51) Int. Cl.
*A61F 2/24* (2006.01)

(52) U.S. Cl. .................................................. 623/2.1

(58) Field of Classification Search .......... 623/2.1–2.24
See application file for complete search history.

(56) References Cited

U.S. PATENT DOCUMENTS 2,832,078 A * 4/1958 Williams .................... 623/2.19

(Continued)

FOREIGN PATENT DOCUMENTS

DE 195 32 846 3/1997

(Continued)

OTHER PUBLICATIONS

U.S. Appl. No. 12/250,163, filed Oct. 13, 2008.

(Continued)

*Primary Examiner*—Suzette J Gherbi
(74) *Attorney, Agent, or Firm*—Jeffrey J. Hohenshell; Mike Jaro

(57) ABSTRACT

A prosthetic valve assembly for use in replacing a deficient native valve comprises a replacement valve supported on an expandable valve support. If desired, one or more anchor may be used. The valve support, which entirely supports the valve annulus, valve leaflets, and valve commissure points, is configured to be collapsible for transluminal delivery and expandable to contact the anatomical annulus of the native valve when the assembly is properly positioned. The anchor engages the lumen wall when expanded and prevents substantial migration of the valve assembly when positioned in place. The prosthetic valve assembly is compressible about a catheter, and restrained from expanding by an outer sheath. The catheter may be inserted inside a lumen within the body, such as the femoral artery, and delivered to a desired location, such as the heart. When the outer sheath is retracted, the prosthetic valve assembly expands to an expanded position such that the valve and valve support expand within the deficient native valve, and the anchor engages the lumen wall.

15 Claims, 25 Drawing Sheets

U.S. PATENT DOCUMENTS

| | | |
|---|---|---|
| 3,334,629 A | 8/1967 | Cohn |
| 3,409,013 A | 11/1968 | Berry |
| 3,540,431 A | 11/1970 | Mobin-Uddin |
| 3,587,115 A | 6/1971 | Shiley |
| 3,628,535 A | 12/1971 | Ostrowsky et al |
| 3,642,004 A | 2/1972 | Osthagen et al |
| 3,657,744 A * | 4/1972 | Ersek .................... 128/898 |
| 3,671,979 A | 6/1972 | Moulopoulos |
| 3,714,671 A | 2/1973 | Edwards et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al |
| 3,874,388 A | 4/1975 | King et al |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos |
| 4,291,420 A | 9/1981 | Reul |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,425,908 A | 1/1984 | Simon |
| 4,470,157 A | 9/1984 | Love |
| 4,501,030 A | 2/1985 | Lane |
| 4,574,803 A | 3/1986 | Storz |
| 4,580,568 A | 4/1986 | Gianturco |
| 4,592,340 A | 6/1986 | Boyles |
| 4,610,688 A | 9/1986 | Silvestrini et al. |
| 4,612,011 A | 9/1986 | Kautzky |
| 4,647,283 A | 3/1987 | Carpentier et al. |
| 4,648,881 A | 3/1987 | Carpentier et al. |
| 4,655,771 A | 4/1987 | Wallsten |
| 4,662,885 A | 5/1987 | DiPisa, Jr. |
| 4,665,906 A | 5/1987 | Jervis |
| 4,681,908 A | 7/1987 | Broderick et al. |
| 4,710,192 A | 12/1987 | Liotta et al. |
| 4,733,665 A | 3/1988 | Palmaz |
| 4,777,951 A | 10/1988 | Cribier et al. |
| 4,787,899 A | 11/1988 | Lazarus |
| 4,796,629 A | 1/1989 | Grayzel |
| 4,797,901 A | 1/1989 | Baykut |
| 4,819,751 A | 4/1989 | Shimada et al. |
| 4,834,755 A | 5/1989 | Silvestrini et al. |
| 4,851,000 A * | 7/1989 | Gupta .................... 623/2.18 |
| 4,856,516 A | 8/1989 | Hillstead |
| 4,872,874 A | 10/1989 | Taheri |
| 4,878,495 A | 11/1989 | Grayzel |
| 4,878,906 A | 11/1989 | Lindemann et al. |
| 4,883,458 A | 11/1989 | Shiber |
| 4,909,252 A | 3/1990 | Goldberger |
| 4,917,102 A | 4/1990 | Miller et al. |
| 4,922,905 A | 5/1990 | Strecker |
| 4,954,126 A | 9/1990 | Wallsten |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,061,273 A | 10/1991 | Yock |
| 5,085,635 A | 2/1992 | Cragg |
| 5,089,015 A | 2/1992 | Ross |
| 5,152,771 A | 10/1992 | Sabbaghian et al. |
| 5,161,547 A | 11/1992 | Tower |
| 5,163,953 A | 11/1992 | Vince |
| 5,167,628 A | 12/1992 | Boyles |
| 5,217,483 A | 6/1993 | Tower |
| 5,232,445 A | 8/1993 | Bonzel |
| 5,272,909 A | 12/1993 | Nguyen et al. |
| 5,295,958 A | 3/1994 | Shturman |
| 5,327,774 A | 7/1994 | Nguyen et al. |
| 5,332,402 A | 7/1994 | Teitelbaum et al. |
| 5,350,398 A | 9/1994 | Pavcnik et al. |
| 5,370,685 A | 12/1994 | Stevens |
| 5,389,106 A | 2/1995 | Tower |
| 5,397,351 A | 3/1995 | Pavcnik et al. |
| 5,411,552 A | 5/1995 | Andersen et al. |
| 5,415,633 A | 5/1995 | Lazarus et al. |
| 5,431,676 A | 7/1995 | Dubrul et al. |
| 5,443,446 A | 8/1995 | Shturman |
| 5,480,424 A | 1/1996 | Cox |
| 5,489,294 A | 2/1996 | McVenes et al. |
| 5,489,297 A | 2/1996 | Duran |
| 5,496,346 A | 3/1996 | Horzewski et al. |
| 5,500,014 A | 3/1996 | Quijano et al. |
| 5,507,767 A | 4/1996 | Maeda et al. |
| 5,545,209 A | 8/1996 | Roberts et al. |
| 5,545,211 A | 8/1996 | An et al. |
| 5,545,214 A | 8/1996 | Stevens |
| 5,554,185 A | 9/1996 | Block et al. |
| 5,575,818 A | 11/1996 | Pinchuk |
| 5,580,922 A | 12/1996 | Park et al. |
| 5,591,195 A | 1/1997 | Taheri et al. |
| 5,609,626 A | 3/1997 | Quijano et al. |
| 5,645,559 A | 7/1997 | Hachtman et al. |
| 5,665,115 A | 9/1997 | Cragg |
| 5,667,523 A | 9/1997 | Bynon et al. |
| 5,674,277 A | 10/1997 | Freitag |
| 5,695,498 A | 12/1997 | Tower |
| 5,702,368 A | 12/1997 | Stevens et al. |
| 5,713,953 A | 2/1998 | Vallana et al. |
| 5,716,417 A * | 2/1998 | Girard et al. ................ 623/2.38 |
| 5,746,709 A | 5/1998 | Rom et al. |
| 5,749,890 A | 5/1998 | Shaknovich |
| 5,766,151 A | 6/1998 | Valley et al. |
| 5,782,809 A | 7/1998 | Umeno et al. |
| 5,800,456 A | 9/1998 | Maeda et al. |
| 5,800,508 A | 9/1998 | Goicoechea et al. |
| 5,817,126 A | 10/1998 | Imran |
| 5,824,041 A | 10/1998 | Lenker |
| 5,824,043 A | 10/1998 | Cottone, Jr. |
| 5,824,053 A | 10/1998 | Khosravi et al. |
| 5,824,056 A | 10/1998 | Rosenberg |
| 5,824,061 A | 10/1998 | Quijano et al. |
| 5,824,064 A | 10/1998 | Taheri |
| 5,840,081 A | 11/1998 | Andersen et al. |
| 5,843,158 A | 12/1998 | Lenker et al. |
| 5,851,232 A | 12/1998 | Lois |
| 5,855,597 A | 1/1999 | Jayaraman |
| 5,855,601 A | 1/1999 | Bessler et al. |
| 5,860,996 A | 1/1999 | Tower |
| 5,861,028 A | 1/1999 | Angell |
| 5,868,783 A | 2/1999 | Tower |
| 5,876,448 A | 3/1999 | Thompson et al. |
| 5,888,201 A | 3/1999 | Stinson et al. |
| 5,891,191 A | 4/1999 | Stinson |
| 5,906,619 A | 5/1999 | Olson et al. |
| 5,907,893 A | 6/1999 | Zadno-Azizi et al. |
| 5,913,842 A | 6/1999 | Boyd et al. |
| 5,925,063 A | 7/1999 | Khosravi |
| 5,944,738 A | 8/1999 | Amplatz et al. |
| 5,951,288 A * | 9/1999 | Sawa .................... 433/173 |
| 5,954,766 A | 9/1999 | Zadno-Azizi et al. |
| 5,957,949 A * | 9/1999 | Leonhardt et al. .......... 623/1.24 |
| 5,968,068 A | 10/1999 | Dehdashtian et al. |

| | | | |
|---|---|---|---|
| 5,984,957 A | 11/1999 | Laptewicz, Jr. et al. |
| 5,997,573 A | 12/1999 | Quijano et al. |
| 6,022,370 A | 2/2000 | Tower |
| 6,027,525 A | 2/2000 | Suh et al. |
| 6,029,671 A | 2/2000 | Stevens et al. |
| 6,042,589 A | 3/2000 | Marianne |
| 6,042,598 A | 3/2000 | Tsugita et al. |
| 6,042,607 A | 3/2000 | Williamson, IV |
| 6,051,014 A | 4/2000 | Jang |
| 6,059,809 A | 5/2000 | Amor et al. |
| 6,110,201 A | 8/2000 | Quijano et al. |
| 6,146,366 A | 11/2000 | Schachar |
| 6,159,239 A | 12/2000 | Greenhalgh |
| 6,162,208 A | 12/2000 | Hipps |
| 6,162,245 A | 12/2000 | Jayaraman |
| 6,168,614 B1 | 1/2001 | Andersen et al. |
| 6,171,335 B1 | 1/2001 | Wheatley et al. |
| 6,200,336 B1 | 3/2001 | Pavcnik et al. |
| 6,203,550 B1 | 3/2001 | Olson |
| 6,210,408 B1 | 4/2001 | Chandrasekaran et al. |
| 6,218,662 B1 | 4/2001 | Tchakarov et al. |
| 6,221,006 B1 | 4/2001 | Dubrul et al. |
| 6,221,091 B1 | 4/2001 | Khosravi |
| 6,241,757 B1 | 6/2001 | An et al. |
| 6,245,102 B1 | 6/2001 | Jayaraman |
| 6,248,116 B1 | 6/2001 | Chevillon |
| 6,258,114 B1 | 7/2001 | Konya et al. |
| 6,258,115 B1 | 7/2001 | Dubrul |
| 6,258,120 B1 | 7/2001 | McKenzie et al. |
| 6,277,555 B1 | 8/2001 | Duran et al. |
| 6,299,637 B1 | 10/2001 | Shaolia et al. |
| 6,302,906 B1 | 10/2001 | Goicoechea et al. |
| 6,309,382 B1 | 10/2001 | Garrison et al. |
| 6,309,417 B1 | 10/2001 | Spence et al. |
| 6,327,772 B1 | 12/2001 | Zadno-Azizi et al. |
| 6,338,735 B1 | 1/2002 | Stevens |
| 6,348,063 B1 | 2/2002 | Yassour et al. |
| 6,350,277 B1 | 2/2002 | Kocur |
| 6,352,708 B1 | 3/2002 | Duran et al. |
| 6,371,983 B1 | 4/2002 | Lane |
| 6,379,383 B1 | 4/2002 | Palmaz et al. |
| 6,380,457 B1 | 4/2002 | Yurek et al. |
| 6,398,807 B1 | 6/2002 | Chouinard et al. |
| 6,409,750 B1 | 6/2002 | Hyodoh et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,475,239 B1 | 11/2002 | Campbell et al. |
| 6,482,228 B1 | 11/2002 | Norred |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,562,031 B2 | 5/2003 | Chandrasekaran et al. |
| 6,562,058 B2 | 5/2003 | Seguin et al. |
| 6,569,191 B1 * | 5/2003 | Hogan ................ 623/1.11 |
| 6,569,196 B1 | 5/2003 | Vesely |
| 6,585,758 B1 | 7/2003 | Chouinard et al. |
| 6,592,546 B1 | 7/2003 | Barbut et al. |
| 6,605,112 B1 | 8/2003 | Moll et al. |
| 6,613,077 B2 | 9/2003 | Gilligan et al. |
| 6,622,604 B1 | 9/2003 | Chouinard et al. |
| 6,632,243 B1 | 10/2003 | Zadno-Azizi et al. |
| 6,635,068 B1 | 10/2003 | Dubrul et al. |
| 6,652,571 B1 | 11/2003 | White et al. |
| 6,652,578 B2 | 11/2003 | Bailey et al. |
| 6,656,213 B2 | 12/2003 | Solem |
| 6,663,663 B2 | 12/2003 | Kim et al. |
| 6,669,724 B2 | 12/2003 | Park et al. |
| 6,673,089 B2 | 1/2004 | Yassour et al. |
| 6,673,109 B2 | 1/2004 | Cox |
| 6,676,698 B2 | 1/2004 | McGuckin, Jr. et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,695,878 B2 | 2/2004 | McGuckin, Jr. et al. |
| 6,702,851 B1 | 3/2004 | Chinn et al. |
| 6,719,789 B2 | 4/2004 | Cox |
| 6,730,118 B2 | 5/2004 | Spenser et al. |
| 6,730,377 B2 | 5/2004 | Wang |
| 6,371,970 B1 | 4/2002 | Khosravi et al. |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,769,434 B2 | 8/2004 | Liddicoat et al. |
| 6,786,925 B1 | 9/2004 | Schoon |
| 6,790,229 B1 | 9/2004 | Berreklouw |
| 6,792,979 B2 | 9/2004 | Konya et al. |
| 6,797,002 B2 | 9/2004 | Spence |
| 6,821,297 B2 | 11/2004 | Snyders |
| 6,830,575 B2 | 12/2004 | Stenzel et al. |
| 6,830,584 B1 | 12/2004 | Seguin |
| 6,830,585 B1 | 12/2004 | Artof |
| 6,846,325 B2 | 1/2005 | Liddicoat |
| 6,866,650 B2 | 3/2005 | Stevens |
| 6,872,223 B2 | 3/2005 | Roberts |
| 6,875,231 B2 | 4/2005 | Anduiza et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 | 6/2005 | Cribier |
| 6,913,600 B2 | 7/2005 | Valley et al. |
| 6,929,653 B2 | 8/2005 | Streeter |
| 6,936,066 B2 | 8/2005 | Palmaz et al. |
| 6,939,365 B1 | 9/2005 | Fogarty et al. |
| 6,951,571 B1 | 10/2005 | Srivastava |
| 6,986,742 B2 | 1/2006 | Hart et al. |
| 6,989,027 B2 | 1/2006 | Allen et al. |
| 6,989,028 B2 | 1/2006 | Lashinski et al. |
| 6,991,649 B2 | 1/2006 | Sievers |
| 7,018,401 B1 | 3/2006 | Hyodoh et al. |
| 7,018,406 B2 * | 3/2006 | Seguin et al. ................ 623/2.1 |
| 7,041,128 B2 | 5/2006 | McGuckin, Jr. et al. |
| 7,044,966 B2 | 5/2006 | Svanidze et al. |
| 7,048,014 B2 | 5/2006 | Hyodoh et al. |
| 7,097,659 B2 | 8/2006 | Woolfson et al. |
| 7,101,396 B2 | 9/2006 | Artof et al. |
| 7,105,016 B2 | 9/2006 | Shiu et al. |
| 7,115,141 B2 | 10/2006 | Menz et al. |
| 7,147,663 B1 | 12/2006 | Berg et al. |
| 7,153,324 B2 | 12/2006 | Case et al. |
| 7,160,319 B2 | 1/2007 | Chouinard et al. |
| 7,175,656 B2 | 2/2007 | Khairkhahan |
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,252,682 B2 | 8/2007 | Seguin |
| 7,300,457 B2 | 11/2007 | Palmaz |
| 7,300,463 B2 | 11/2007 | Liddicoat |
| 7,316,706 B2 | 1/2008 | Bloom et al. |
| 7,329,278 B2 | 2/2008 | Seguin |

| | | | | | | |
|---|---|---|---|---|---|---|
| 7,335,218 | B2 | 2/2008 | Wilson et al. | 2003/0199971 A1 | 10/2003 | Tower et al. |
| 7,338,520 | B2 | 3/2008 | Bailey et al. | 2003/0199972 A1 | 10/2003 | Zadno-Azizi et al. |
| 7,374,571 | B2 | 5/2008 | Pease et al. | 2003/0212410 A1 | 11/2003 | Stenzel et al. |
| 7,381,218 | B2 | 6/2008 | Shreck | 2003/0212452 A1 | 11/2003 | Zadno-Azizi et al. |
| 7,384,411 | B1 | 6/2008 | Condado | 2003/0212454 A1 | 11/2003 | Scott et al. |
| 7,429,269 | B2 | 9/2008 | Schwammenthal et al. | 2004/0034411 A1 | 2/2004 | Quijano et al. |
| 7,442,204 | B2 | 10/2008 | Schwammenthal et al. | 2004/0039436 A1 | 2/2004 | Spenser et al. |
| 7,462,191 | B2 | 12/2008 | Spenser et al. | 2004/0049224 A1 | 3/2004 | Buehlmann et al. |
| 7,470,284 | B2 | 12/2008 | Lambrecht et al. | 2004/0049262 A1 | 3/2004 | Obermiller et al. |
| 7,481,838 | B2 | 1/2009 | Carpentier et al. | 2004/0049266 A1 | 3/2004 | Anduiza et al. |
| 7,544,206 | B2 | 6/2009 | Cohn et al. | 2004/0082904 A1 | 4/2004 | Houde et al. |
| 7,556,646 | B2 | 7/2009 | Yang et al. | 2004/0088045 A1 | 5/2004 | Cox |
| 7,682,390 | B2 | 3/2010 | Seguin | 2004/0093005 A1 | 5/2004 | Durcan |
| 7,780,726 | B2 | 8/2010 | Seguin | 2004/0093060 A1 | 5/2004 | Seguin et al. |
| 7,806,919 | B2 | 10/2010 | Bloom et al. | 2004/0097788 A1 | 5/2004 | Mourlas et al. |
| 2001/0001314 | A1 | 5/2001 | Davison et al. | 2004/0098112 A1 | 5/2004 | DiMatteo et al. |
| 2001/0002445 | A1 | 5/2001 | Vesely | 2004/0106976 A1 | 6/2004 | Bailey et al. |
| 2001/0007956 | A1 | 7/2001 | Letac et al. | 2004/0106990 A1 | 6/2004 | Spence et al. |
| 2001/0010017 | A1 | 7/2001 | Letac et al. | 2004/0111096 A1 | 6/2004 | Tu et al. |
| 2001/0011189 | A1 | 8/2001 | Drasler et al. | 2004/0116951 A1 | 6/2004 | Rosengart |
| 2001/0021872 | A1 | 9/2001 | Bailey et al. | 2004/0117004 A1 | 6/2004 | Osborne et al. |
| 2001/0025196 | A1 | 9/2001 | Chinn et al. | 2004/0122468 A1 | 6/2004 | Yodfat et al. |
| 2001/0032013 | A1 | 10/2001 | Marton | 2004/0122516 A1 | 6/2004 | Fogarty |
| 2001/0039450 | A1 | 11/2001 | Pavcnik et al. | 2004/0127979 A1 | 7/2004 | Wilson |
| 2001/0041928 | A1 | 11/2001 | Pavcnik et al. | 2004/0138742 A1 | 7/2004 | Myers et al. |
| 2001/0044647 | A1 | 11/2001 | Pinchuk et al. | 2004/0138743 A1 | 7/2004 | Myers et al. |
| 2002/0010508 | A1 | 1/2002 | Chobotov | 2004/0153146 A1 | 8/2004 | Lashinski et al. |
| 2002/0029014 | A1 | 3/2002 | Jayaraman | 2004/0167573 A1 | 8/2004 | Williamson |
| 2002/0032480 | A1 | 3/2002 | Spence et al. | 2004/0167620 A1 | 8/2004 | Ortiz |
| 2002/0032481 | A1 | 3/2002 | Gabbay | 2004/0186563 A1 | 9/2004 | Iobbi |
| 2002/0035396 | A1 | 3/2002 | Heath | 2004/0193261 A1 | 9/2004 | Berreklouw |
| 2002/0042650 | A1 | 4/2002 | Vardi et al. | 2004/0210240 A1 | 10/2004 | Saint |
| 2002/0052651 | A1 | 5/2002 | Myers et al. | 2004/0210304 A1 | 10/2004 | Seguin et al. |
| 2002/0058995 | A1 | 5/2002 | Stevens | 2004/0210307 A1 | 10/2004 | Khairkhahan |
| 2002/0072789 | A1 | 6/2002 | Hackett et al. | 2004/0215333 A1 | 10/2004 | Duran |
| 2002/0077696 | A1 | 6/2002 | Zadno-Azizi et al. | 2004/0215339 A1 | 10/2004 | Drasler et al. |
| 2002/0095209 | A1 | 7/2002 | Zadno-Azizi et al. | 2004/0225353 A1 | 11/2004 | McGuckin, Jr. |
| 2002/0099439 | A1 | 7/2002 | Schwartz et al. | 2004/0225354 A1 | 11/2004 | Allen |
| 2002/0103533 | A1 | 8/2002 | Langberg et al. | 2004/0254636 A1 | 12/2004 | Flagle et al. |
| 2002/0107565 | A1 | 8/2002 | Greenhalgh | 2004/0260394 A1 | 12/2004 | Douk et al. |
| 2002/0111674 | A1 | 8/2002 | Chouinard et al. | 2004/0267357 A1 | 12/2004 | Allen et al. |
| 2002/0123802 | A1 | 9/2002 | Snyders | 2005/0010246 A1 | 1/2005 | Streeter |
| 2002/0133183 | A1 | 9/2002 | Lentz et al. | 2005/0010285 A1 | 1/2005 | Lambrecht et al. |
| 2002/0138138 | A1 | 9/2002 | Yang | 2005/0010287 A1 | 1/2005 | Macoviak |
| 2002/0151970 | A1 | 10/2002 | Garrison et al. | 2005/0015112 A1 | 1/2005 | Cohn et al. |
| 2002/0161392 | A1 | 10/2002 | Dubrul | 2005/0027348 A1 | 2/2005 | Case et al. |
| 2002/0161394 | A1 | 10/2002 | Macoviak et al. | 2005/0033398 A1 | 2/2005 | Seguin |
| 2002/0193871 | A1 | 12/2002 | Beyersdorf et al. | 2005/0043790 A1 | 2/2005 | Seguin |
| 2003/0014104 | A1 | 1/2003 | Cribier | 2005/0049692 A1 | 3/2005 | Numamoto |
| 2003/0023300 | A1 | 1/2003 | Bailey et al. | 2005/0049696 A1 | 3/2005 | Siess |
| 2003/0023303 | A1 | 1/2003 | Palmaz et al. | 2005/0055088 A1 | 3/2005 | Liddicoat et al. |
| 2003/0028247 | A1 | 2/2003 | Cali | 2005/0060029 A1 | 3/2005 | Le |
| 2003/0036791 | A1 | 2/2003 | Bonhoeffer et al. | 2005/0060030 A1 | 3/2005 | Lashinski et al. |
| 2003/0040771 | A1 | 2/2003 | Hyodoh et al. | 2005/0075584 A1 | 4/2005 | Cali |
| 2003/0040772 | A1 | 2/2003 | Hyodoh et al. | 2005/0075712 A1 | 4/2005 | Biancucci |
| 2003/0040792 | A1 | 2/2003 | Gabbay | 2005/0075717 A1 | 4/2005 | Nguyen |
| 2003/0050694 | A1 | 3/2003 | Yang et al. | 2005/0075719 A1 | 4/2005 | Bergheim |
| 2003/0055495 | A1 | 3/2003 | Pease et al. | 2005/0075724 A1 | 4/2005 | Svanidze |
| 2003/0065386 | A1 | 4/2003 | Weadock | 2005/0075727 A1 | 4/2005 | Wheatley |
| 2003/0069492 | A1 | 4/2003 | Abrams et al. | 2005/0075730 A1 | 4/2005 | Myers |
| 2003/0109924 | A1 | 6/2003 | Cribier | 2005/0075731 A1 | 4/2005 | Artof |
| 2003/0125795 | A1 | 7/2003 | Pavcnik et al. | 2005/0085841 A1 | 4/2005 | Eversull et al. |
| 2003/0130726 | A1 | 7/2003 | Thorpe et al. | 2005/0085842 A1 | 4/2005 | Eversull et al. |
| 2003/0130729 | A1 | 7/2003 | Paniagua et al. | 2005/0085843 A1 | 4/2005 | Opolski et al. |
| 2003/0139804 | A1 | 7/2003 | Hankh et al. | 2005/0085890 A1 | 4/2005 | Rasmussen et al. |
| 2003/0149475 | A1 | 8/2003 | Hyodoh et al. | 2005/0085900 A1 | 4/2005 | Case et al. |
| 2003/0149476 | A1 | 8/2003 | Damm et al. | 2005/0096568 A1 | 5/2005 | Kato |
| 2003/0149478 | A1 | 8/2003 | Figulla et al. | 2005/0096692 A1 | 5/2005 | Linder et al. |
| 2003/0153974 | A1 | 8/2003 | Spenser et al. | 2005/0096724 A1 | 5/2005 | Stenzel et al. |
| 2003/0181850 | A1 | 9/2003 | Diamond et al. | 2005/0096734 A1 | 5/2005 | Majercak et al. |
| 2003/0191519 | A1 | 10/2003 | Lombardi et al. | 2005/0096735 A1 | 5/2005 | Hojeibane et al. |
| 2003/0199913 | A1 | 10/2003 | Dubrul et al. | 2005/0096736 A1 | 5/2005 | Osse et al. |
| 2003/0199963 | A1 | 10/2003 | Tower et al. | 2005/0096738 A1 | 5/2005 | Cali et al. |

| | | | | | |
|---|---|---|---|---|---|
| 2005/0107871 A1 | 5/2005 | Realyvasquez et al. | 2007/0239254 A1 | 10/2007 | Marchand et al. |
| 2005/0113910 A1 | 5/2005 | Paniagua | 2007/0239265 A1 | 10/2007 | Birdsall |
| 2005/0119688 A1 | 6/2005 | Berheim | 2007/0239266 A1 | 10/2007 | Birdsall |
| 2005/0131438 A1 | 6/2005 | Cohn | 2007/0239269 A1 | 10/2007 | Dolan et al. |
| 2005/0137686 A1 | 6/2005 | Salahieh | 2007/0239271 A1 | 10/2007 | Nguyen |
| 2005/0137688 A1 | 6/2005 | Salahieh et al. | 2007/0239273 A1 | 10/2007 | Allen |
| 2005/0137692 A1 | 6/2005 | Haug | 2007/0244544 A1 | 10/2007 | Birdsall et al. |
| 2005/0137695 A1 | 6/2005 | Salahieh | 2007/0244545 A1 | 10/2007 | Birdsall et al. |
| 2005/0137701 A1 | 6/2005 | Salahieh | 2007/0244546 A1 | 10/2007 | Francis |
| 2005/0143809 A1 | 6/2005 | Salahieh | 2007/0244553 A1 | 10/2007 | Rafiee et al. |
| 2005/0148997 A1 | 7/2005 | Valley et al. | 2007/0244554 A1 | 10/2007 | Rafiee et al. |
| 2005/0165477 A1 | 7/2005 | Anduiza et al. | 2007/0244555 A1 | 10/2007 | Rafiee et al. |
| 2005/0187616 A1 | 8/2005 | Realyvasquez | 2007/0244556 A1 | 10/2007 | Rafiee et al. |
| 2005/0203549 A1 | 9/2005 | Realyvasquez | 2007/0244557 A1 | 10/2007 | Rafiee et al. |
| 2005/0203605 A1 | 9/2005 | Dolan | 2007/0250160 A1 | 10/2007 | Rafiee |
| 2005/0203618 A1 | 9/2005 | Sharkawy | 2007/0255394 A1 | 11/2007 | Ryan |
| 2005/0222674 A1 | 10/2005 | Paine | 2007/0255396 A1 | 11/2007 | Douk et al. |
| 2005/0228495 A1 | 10/2005 | Macoviak | 2007/0288000 A1 | 12/2007 | Bonan |
| 2005/0234546 A1 | 10/2005 | Nugent | 2008/0004696 A1 | 1/2008 | Vesely |
| 2005/0240200 A1 | 10/2005 | Bergheim | 2008/0009940 A1 | 1/2008 | Cribier |
| 2005/0240263 A1 | 10/2005 | Fogarty et al. | 2008/0015671 A1 | 1/2008 | Bonhoeffer |
| 2005/0261759 A1 | 11/2005 | Lambrecht et al. | 2008/0021552 A1 | 1/2008 | Gabbay |
| 2005/0283962 A1 | 12/2005 | Boudjemline | 2008/0048656 A1 | 2/2008 | Tan |
| 2006/0004439 A1 | 1/2006 | Spenser et al. | 2008/0065001 A1 | 3/2008 | Marchand et al. |
| 2006/0009841 A1 | 1/2006 | McGuckin et al. | 2008/0065206 A1 | 3/2008 | Liddicoat |
| 2006/0052867 A1 | 3/2006 | Revuelta et al. | 2008/0071361 A1 | 3/2008 | Tuval et al. |
| 2006/0058775 A1 | 3/2006 | Stevens et al. | 2008/0071362 A1 | 3/2008 | Tuval et al. |
| 2006/0089711 A1 | 4/2006 | Dolan | 2008/0071363 A1 | 3/2008 | Tuval et al. |
| 2006/0100685 A1 | 5/2006 | Seguin et al. | 2008/0071366 A1 | 3/2008 | Tuval et al. |
| 2006/0116757 A1 | 6/2006 | Lashinski et al. | 2008/0071368 A1 | 3/2008 | Tuval et al. |
| 2006/0135964 A1 | 6/2006 | Vesely | 2008/0077234 A1 | 3/2008 | Styrc |
| 2006/0142848 A1 | 6/2006 | Gabbay | 2008/0082165 A1 | 4/2008 | Wilson et al. |
| 2006/0167474 A1 | 7/2006 | Bloom et al. | 2008/0082166 A1 | 4/2008 | Styrc et al. |
| 2006/0178740 A1 | 8/2006 | Stacchino et al. | 2008/0133003 A1 | 6/2008 | Seguin et al. |
| 2006/0195134 A1 | 8/2006 | Crittenden | 2008/0140189 A1 | 6/2008 | Nguyen et al. |
| 2006/0206192 A1 | 9/2006 | Tower et al. | 2008/0147105 A1 | 6/2008 | Wilson et al. |
| 2006/0206202 A1 | 9/2006 | Bonhoefer et al. | 2008/0147180 A1 | 6/2008 | Ghione et al. |
| 2006/0247763 A1 | 11/2006 | Slater | 2008/0147181 A1 | 6/2008 | Ghione et al. |
| 2006/0259134 A1 | 11/2006 | Schwammenthal et al. | 2008/0147182 A1 | 6/2008 | Righini et al. |
| 2006/0259136 A1 | 11/2006 | Nguyen et al. | 2008/0154356 A1 | 6/2008 | Obermiller et al. |
| 2006/0259137 A1 | 11/2006 | Artof et al. | 2008/0161910 A1 | 7/2008 | Revuelta et al. |
| 2006/0265056 A1 | 11/2006 | Nguyen et al. | 2008/0161911 A1 | 7/2008 | Revuelta et al. |
| 2006/0271166 A1 | 11/2006 | Thill et al. | 2008/0183273 A1 | 7/2008 | Mesana et al. |
| 2006/0271175 A1 | 11/2006 | Woolfson et al. | 2008/0188928 A1 | 8/2008 | Salahieh et al. |
| 2006/0276874 A1 | 12/2006 | Wilson et al. | 2008/0215143 A1 | 9/2008 | Seguin et al. |
| 2006/0282161 A1 | 12/2006 | Huynh et al. | 2008/0215144 A1 | 9/2008 | Ryan et al. |
| 2007/0005129 A1 | 1/2007 | Damm et al. | 2008/0228254 A1 | 9/2008 | Ryan |
| 2007/0005131 A1 | 1/2007 | Taylor | 2008/0228263 A1 | 9/2008 | Ryan |
| 2007/0010878 A1 | 1/2007 | Raffiee et al. | 2008/0234797 A1 | 9/2008 | Styrc |
| 2007/0016286 A1 | 1/2007 | Case et al. | 2008/0243246 A1 | 10/2008 | Ryan et al. |
| 2007/0027518 A1 | 2/2007 | Herrmann et al. | 2008/0255651 A1 | 10/2008 | Dwork |
| 2007/0027533 A1 | 2/2007 | Douk | 2008/0255660 A1 | 10/2008 | Guyenot et al. |
| 2007/0043435 A1 | 2/2007 | Seguin et al. | 2008/0255661 A1 | 10/2008 | Straubinger et al. |
| 2007/0051377 A1 | 3/2007 | Douk et al. | 2008/0262593 A1 | 10/2008 | Ryan et al. |
| 2007/0073392 A1 | 3/2007 | Heynick-Janitz | 2009/0005863 A1 | 1/2009 | Goetz et al. |
| 2007/0078509 A1 | 4/2007 | Lotfy et al. | 2009/0012600 A1 | 1/2009 | Styrc et al. |
| 2007/0078510 A1 | 4/2007 | Ryan | 2009/0048656 A1 | 2/2009 | Wen |
| 2007/0088431 A1 | 4/2007 | Bourang et al. | 2009/0054976 A1 | 2/2009 | Tuval et al. |
| 2007/0093869 A1 | 4/2007 | Bloom et al. | 2009/0069886 A1 | 3/2009 | Suri et al. |
| 2007/0100439 A1 | 5/2007 | Cangialosi | 2009/0069887 A1 | 3/2009 | Righini et al. |
| 2007/0100440 A1 | 5/2007 | Figulla | 2009/0069889 A1 | 3/2009 | Suri et al. |
| 2007/0100449 A1 | 5/2007 | O'Neil et al. | 2009/0138079 A1 | 5/2009 | Tuval et al. |
| 2007/0112415 A1 | 5/2007 | Bartlett | 2009/0164004 A1 | 6/2009 | Cohn |
| 2007/0162102 A1 | 7/2007 | Ryan et al. | 2009/0164006 A1 | 6/2009 | Seguin et al. |
| 2007/0162113 A1 | 7/2007 | Sharkawy et al. | 2009/0171447 A1 | 7/2009 | VonSeggesser |
| 2007/0185513 A1 | 8/2007 | Woolfson et al. | 2009/0192585 A1 | 7/2009 | Bloom et al. |
| 2007/0203391 A1 | 8/2007 | Bloom et al. | 2009/0192586 A1 | 7/2009 | Tabor et al. |
| 2007/0225681 A1 | 9/2007 | House | 2009/0192591 A1 | 7/2009 | Ryan et al. |
| 2007/0232898 A1 | 10/2007 | Huynh et al. | 2009/0198316 A1 | 8/2009 | Laske et al. |
| 2007/0233228 A1 | 10/2007 | Eberhardt et al. | 2009/0216310 A1 | 8/2009 | Straubinger et al. |
| 2007/0233237 A1 | 10/2007 | Krivoruchko | 2009/0216312 A1 | 8/2009 | Straubinger et al. |
| 2007/0233238 A1 | 10/2007 | Huynh et al. | 2009/0216313 A1 | 8/2009 | Straubinger et al. |
| 2007/0238979 A1 | 10/2007 | Huynh et al. | 2009/0240264 A1 | 9/2009 | Tuval et al. |

| | | | |
|---|---|---|---|
| 2009/0240320 A1 | 9/2009 | Tuval | |
| 2009/0281619 A1 | 11/2009 | Le et al. | |
| 2010/0004740 A1 | 1/2010 | Seguin et al. | |
| 2010/0030328 A1 | 2/2010 | Seguin et al. | |
| 2010/0036485 A1 | 2/2010 | Seguin | |
| 2010/0069852 A1 | 3/2010 | Kelley | |
| 2010/0094411 A1 | 4/2010 | Tuval et al. | |
| 2010/0100167 A1 | 4/2010 | Bortlein et al. | |
| 2010/0131054 A1 | 5/2010 | Tuval et al. | |
| 2010/0137979 A1 | 6/2010 | Tuval et al. | |
| 2010/0145439 A1 | 6/2010 | Seguin et al. | |
| 2010/0152840 A1 | 6/2010 | Seguin et al. | |
| 2010/0198346 A1 | 8/2010 | Keogh et al. | |
| 2010/0234940 A1 | 9/2010 | Dolan | |
| 2010/0256723 A1 | 10/2010 | Murray | |

FOREIGN PATENT DOCUMENTS

| | | |
|---|---|---|
| DE | 195 46 692 C2 | 6/1997 |
| DE | 195 46692 A1 | 6/1997 |
| DE | 198 57 887 A1 | 7/2000 |
| DE | 199 07 646 | 8/2000 |
| DE | 100 48 814 | 9/2000 |
| DE | 10010074 | 10/2001 |
| DE | 100 49 812 | 4/2002 |
| DE | 100 49 813 | 4/2002 |
| DE | 100 49 815 | 4/2002 |
| EP | 0103546 | 3/1984 |
| EP | 0597967 | 12/1994 |
| EP | 0850607 | 7/1998 |
| EP | 1057459 A1 | 6/2000 |
| EP | 1057460 A1 | 6/2000 |
| EP | 1088529 | 4/2001 |
| EP | 1255510 | 11/2002 |
| EP | 0937439 B1 | 9/2003 |
| EP | 1340473 | 9/2003 |
| EP | 0819013 | 6/2004 |
| FR | 2 800 984 | 11/1999 |
| FR | 2788217 | 12/1999 |
| FR | 2 815 844 | 10/2000 |
| GB | 2056023 | 3/1981 |
| GB | 2433700 | 12/2007 |
| SU | 1271508 | 11/1986 |
| WO | 91/017720 | 11/1991 |
| WO | 93/001768 | 2/1993 |
| WO | 95/29640 | 11/1995 |
| WO | 98/14137 | 4/1998 |
| WO | 98/29057 | 7/1998 |
| WO | 99/33414 | 7/1999 |
| WO | 00/41652 | 7/2000 |
| WO | 00/44313 | 8/2000 |
| WO | 00/47136 | 8/2000 |
| WO | 00/47139 | 8/2000 |
| WO | 01/35870 | 5/2001 |
| WO | 01/49213 | 7/2001 |
| WO | 01/54625 | 8/2001 |
| WO | 01/62189 | 8/2001 |
| WO | 01/64137 | 9/2001 |
| WO | 01/76510 | 10/2001 |
| WO | 02/22054 | 3/2002 |
| WO | 02/36048 | 5/2002 |
| WO | 02/41789 | 5/2002 |
| WO | 02/43620 | 6/2002 |
| WO | 02/47575 | 6/2002 |
| WO | 02/49540 | 6/2002 |
| WO | 03/003943 | 1/2003 |
| WO | 03/003949 | 1/2003 |
| WO | 03/011195 | 2/2003 |
| WO | 03/030776 | 4/2003 |
| WO | 2004/019811 | 3/2004 |
| WO | 2004/019825 | 3/2004 |
| WO | 2004/023980 | 3/2004 |
| WO | 2004/041126 | 5/2004 |
| WO | 2004/058106 | 7/2004 |
| WO | 2004/089250 | 10/2004 |
| WO | 2005/004753 | 1/2005 |
| WO | 2005/027790 | 3/2005 |
| WO | 2005/046528 | 5/2005 |
| WO | 2008/047354 | 4/2008 |
| WO | 2008/100599 | 8/2008 |
| WO | 2008/150529 | 12/2008 |
| WO | 2009/002548 | 12/2008 |
| WO | 2009/045338 | 4/2009 |
| WO | 2009/061389 | 5/2009 |
| WO | 2009/091509 | 7/2009 |

OTHER PUBLICATIONS

U.S. Appl. No. 61/192,199, filed Sep. 15, 2008.
U.S. Appl. No. 12/253,858, filed Oct. 17, 2008.
U.S. Appl. No. 12/596,343, filed Apr. 14, 2008.
U.S. Appl. No. 61/129,170, filed Jun. 9, 2008.
Andersen, H.R. et al, "Transluminal implantation of artificial heart valves. Description of a new expandable aortic valve and initial results with implantation by catheter technique in closed chest pigs." Euro. Heart J. (1992) 13:704-708.
Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.
Bailey, "Percutaneous Expandable Prosthetic Valves," in: Topol EJ, ed. Textbook of Interventional Cardiology. vol. II. Second edition. WB Saunders, Philadelphia, 1994:1268-1276.
Block, et al., "Percutaneous Approaches to Valvular Heart Disease," Current Cardiology Reports, vol. 7 (2005) pp. 108-113.
Bonhoeffer, et al, "Percutaneous Insertion of the Pulmonary Valve," Journal of the American College of Cardiology (United States), May 15, 2002, pp. 1664-1669.
Bonhoeffer, et al, "Percutaneous Mitral Valve Dilatation with the Multi-Track System," Catheterization and Cardiovascular Interventions—Official Journal of the Society for Cardiac Angiography & Interventions (United States), Oct. 1999, pp. 178-183.
Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.
Bonhoeffer, et al, "Technique and Results of Percutaneous Mitral Valvuloplasty With the Multi-Track System," Journal of Interventional Cardiology (United States), 200, pp. 263-268.
Bonhoeffer, et al, "Transcatheter Implantation of a Bovine Valve in Pulmonary Position: a Lamb Study," Circulation (United States), Aug. 15, 2000, pp. 813-816.
Boudjemline, et al, "Images in Cardiovascular Medicine. Percutaneous Aortic Valve Replacement in Animals," Circulation (United States), Mar. 16, 2004, 109, p. e161.
Boudjemline, et al, "Is Percutaneous Implantation of a Bovine Venous Valve in the Inferior Vena Cava a Reliable Technique to Treat Chronic Venous Insufficiency Syndrome?" Medical Science Monitor—International Medical Journal of Experimental and Clinical Research (Poland), Mar. 2004, pp. BR61-BR66.
Boudjemline, et al, "Off-pump Replacement of the Pulmonary Valve in Large Right Ventricular Outflow Tracts: a Hybrid Approach," Journal of Thoracic and Cardiovascular Surgery (United States), Apr. 2005, pp. 831-837.

Boudjemline, et al, "Percutaneous Aortic Valve Replacement: Will We Get There?" Heart (British Cardiac Society) (England), Dec. 2001, pp. 705-706.

Boudjemline, et al, "Percutaneous Closure of a Paravalvular Mitral Regurgitation with Amplatzer and Coil Prostheses," Archives des Maladies du Coeur Et Des Vaisseaux (France), May 2002, pp. 483-486.

Boudjemline, et al, "Percutaneous Implantation of a Biological Valve in the Aorta to Treat Aortic Valve Insufficiency—a Sheep Study," Medical Science Monitor—International Medical Journal of Experimental and Clinical Research (Poland), Apr. 2002, pp. BR113-BR116.

Boudjemline, et al, "Percutaneous Implantation of a Biological Valve in Aortic Position: Preliminary Results in a Sheep Study," European Heart Journal 22, Sep. 2001, p. 630.

Boudjemline, et al, "Percutaneous Implantation of a Valve in the Descending Aorta in Lambs," European Heart Journal (England), Jul. 2002, pp. 1045-1049.

Boudjemline, et al, "Percutaneous Pulmonary Valve Replacement in a Large Right Ventricular Outflow Tract: an Experimental Study," Journal of the American College of Cardiology (United States), Mar. 17, 2004, pp. 1082-1087.

Boudjemline, et al, "Percutaneous Valve Insertion: a New Approach," Journal of Thoracic and Cardiovascular Surgery (United States), Mar. 2003, pp. 741-742.

Boudjemline, et al, "Stent Implantation Combined with a Valve Replacement to Treat Degenerated Right Ventricle to Pulmonary Artery Prosthetic Conduits," European Heart Journal 22, Sep. 2001, p. 355.

Boudjemline, et al, "Steps Toward Percutaneous Aortic Valve Replacement," Circulation (United States), Feb. 12, 2002, pp. 775-778.

Boudjemline, et al, "The Percutaneous Implantable Heart Valve," Progress in Pediatric Cardiology (Ireland), 2001, pp. 89-93.

Boudjemline, et al, "Transcatheter Reconstruction of the Right Heart," Cardiology in the Young (England), Jun. 2003, pp. 308-311.

Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.

Cribier, A. et al, "Percutaneous Transcatheter Implantation of an Aortic Valve Prosthesis for Calcific Aortic Stenosis: First Human Case Description," Circulation (2002) 3006-3008.

Davidson et al., "Percutaneous therapies for valvular heart disease," Cardiovascular Pathology 15 (2006) 123-129.

Hanzel, et al., "Complications of percutaneous aortic valve replacement: experience with the Criber-Edwards™ percutaneous heart valve," EuroIntervention Supplements (2006), I (Supplement A) A3-A8.

Huber, et al., "Do Valved Stents Compromise Coronary Flow?" Eur. J. Cardiothorac. Surg. 2004;25:754-759.

Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.

Khambadkone, et al, "Percutaneous Implantation of Pulmonary Valves," Expert Review of Cardiovascular Therapy (England), Nov. 2003, pp. 541-548.

Khambadkone, et al, "Percutaneous Pulmonary Valve Implantation: Early and Medium Term Results," Circulation 108 (17 Supplement), Oct. 28, 2003, p. IV-375.

Khambadkone, et al, "Percutaneous Pulmonary Valve Implantation: Impact of Morphology on Case Selection," Circulation 108 (17 Supplement), Oct. 28, 2003, p. IV-642-IV-643.

Lutter, et al, "Percutaneous Aortic Valve Replacement: an Experimental Study. I. Studies on Implantation," The Journal of Thoracic and Cardiovascular Surgery, Apr. 2002, pp. 768-776.

Lutter, et al, "Percutaneous Valve Replacement: Current State and Future Prospects," Annals of Thoracic Surgery (Netherlands), Dec. 2004, pp. 2199-2206.

Medtech Insight, "New Frontiers in Heart Valve Disease," vol. 7, No. 8 (2005).

Palacios, "Percutaneous Valve Replacement and Repair, Fiction or Reality?" Journal of American College of Cardiology, vol. 44, No. 8 (2004) pp. 1662-1663.

Ruiz, "Transcathether Aortic Valve Implantation and Mitral Valve Repair: State of the Art," Pediatric Cardiology, vol. 26, No. 3 (2005).

Saliba, et al, "Treatment of Obstructions of Prosthetic Conduits by Percutaneous Implantation of Stents," Archives des Maldies du Coeur et des Vaisseaux (France), 1999, pp. 591-596.

Webb, et al., "Percutaneous Aortic Valve Implantation Retrograde from the Femoral Artery," Circulation (2006), 113;842-850.

Yonga, et al, "Effect of Percutaneous Balloon Mitral Valvotomy on Pulmonary Venous Flow in Severe Mitral Stenosis," East African Medical Journal (Kenya), Jan. 1999, pp. 28-30.

Yonga, et al, "Percutaneous Balloon Mitral Valvotomy: Initial Experience in Nairobi Using a New Multi-Track Catheter System," East African Medical Journal (Kenya), Feb. 1999, pp. 71-74.

Yonga, et al, "Percutaneous Transluminal Balloon Valvuloplasty for Pulmonary Valve Stenosis: Report on Six Cases," East African Medical Journal (Kenya), Apr. 1994, pp. 232-235.

Yonga, et al, "Percutaneous Transvenous Mitral Commissurotomy in Juvenile Mitral Stenosis," East African Medical Journal (Kenya), Apr. 2003, pp. 172-174.

Commeau et al, "Percutaneous balloon dilatation of calcific aortic valve stenosis: anatomical and haemodynamic evaluation," 1988, British Heart Journal, 59:227-238.

Stassano et al., "Mid-term results of the valve-on-valve technique for bioprosthetic failure," Eur. J. Cardiothorac. Surg. 2000; 18:453-457.

Expert report of Dr. Nigel Buller, dated Jan. 12, 2009, Edwards' United Kingdom action for invalidity, Claim No. HC 08CO0934 (83 pages).

Expert report of Dr. Nigel Buller, non-confidential annex—infringement, dated Jan. 12, 2009, Edwards' United Kingdom action for invalidity, Claim No. HC 08CO0934 (12 pages).

Expert report of Dr. Rodolfo Quijano, dated Jan. 9, 2009, Edwards' United Kingdom action for invalidity, Claim No. HC 08CO0934 (18 pages).

First Expert report of Prof. David Williams, dated Jan. 12, 2009, Edwards' United Kingdom action for invalidity, Claim No. HC 08CO0934 (41 pages).

First Expert report of Prof. Martin Rothman, dated Jan. 12, 2009, Edwards' United Kingdom action for invalidity, Claim No. HC 08CO0934 (64 pages).

Fourth Expert report of Prof. Martin Rothman, dated Apr. 22, 2009, Edwards' United Kingdom action for invalidity, Claim No. HC 08CO0934 (10 pages).
Second Expert report of Dr. Nigel Buller, dated Feb. 25, 2009, Edwards' United Kingdom action for invalidity, Claim No. HC 08CO0934 (24 pages).
Second Expert report of Dr. Rodolfo Quijano, dated Feb. 26, 2009, Edwards' United Kingdom action for invalidity, Claim No. HC 08CO0934 (6 pages).
Second Expert report of Prof. David Williams, dated Feb. 5, 2009, Edwards' United Kingdom action for invalidity, Claim No. HC 08CO0934 (15 pages).
Second Expert report of Prof. Martin Rothman, dated Feb. 5, 2009, Edwards' United Kingdom action for invalidity, Claim No. HC 08CO0934 (11 pages).
Third Expert report of Dr. Nigel Buller, dated Apr. 21, 2009, Edwards' United Kingdom action for invalidity, Claim No. HC 08CO0934 (6 pages).
Third Expert report of Dr. Rudolfo Quijano, dated Apr. 27, 2009, Edwards' United Kingdom action for invalidity, Claim No. HC 08CO0934 (3 pages).
Third Expert report of Prof. David Williams, dated Apr. 22, 2009, Edwards' United Kingdom action for invalidity, Claim No. HC 08CO0934 (9 pages).
Pavcnik et al., "Aortic and venous valve for percutaneous insertion," Min. Invas. Ther. & Allied Techol. 2000, vol. 9, pp. 287-292.
First Expert report of Dr. Nigel Person Buller (30 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
Second Expert report of Dr. Nigel Person Buller (5 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
Drawing by Dr. Buller (Edwards Expert) of his interpretation of the "higher stent" referred to at col. 8, lines 13-222 of Andersen EP 592410B1 (1 page), *Corevalve, Inc. v. Edwards Lifesciences AG and Edwards Lifesciences PVT, Inc.*, High Court of Justice—Chancery Division Patents Court, United Kingdom, Case No. HC-07-C01243.
Drawing by Dr. Buller (Edwards Expert) of "higher stent" on the schematic representation of the aortic valve area set out in Figure 2 of Rothman's first expert report (1 page), *Corevalve, Inc. v. Edwards Lifesciences AG and Edwards Lifesciences PVT, Inc.*, High Court of Justice—Chancery Division Patents Court, United Kingdom, Case No. HC-07-C01243.
First Expert report of Professor John R.4 Pepper (20 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
Second Expert report of Professor John R. Pepper (3 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
First Expert report of Dr. Anthony C. Lunn (7 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
First Witness statement of Stanton Rowe (9 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
Second Witness statement of Stanton Rowe (3 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
PVT slides naming Alain Cribier, Martin Leon, Stan Rabinovich and Stanton Rowe (16 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
First Expert report of Professor Martin Terry Rothman (75 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
Reply Expert report of Professor Martin Terry Rothman (9 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
First Expert report of Richard A. Hillstead (41 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
Reply Expert report of Richard A. Hillstead (9 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.
Pelton et al, Medical Uses of Nitinol, Materials Science Forum vols. 327-328 pp. 63-70. (2000)
Trial Transcripts, *Edwards Lifesciences AG and Edwards Lifesciences, LLC.v. Medtronic Core Valve LLC*, United States District Court for the District of Delaware, Civil Action No. 1:08-CV-00091-GMSM, Mar. 23, 2010-Apr. I, 2010.
Affidavit of Michael D. Gadeberg, Jul. 8, 2010-Apr. 1, 2010.
Slide Deck for Plaintiff's Closing Arguments in *Edwards Lifesciences AG and Edwards Lifesciences, LLC. V. Medtronic Core Valve LLC*, United States District Court for the District of Delaware, Civil Actoin No. 1:08-CV-00091-GMS, Apr. 1, 2010 (107 pages).
Response to Restriction Requirement, U.S. Appl. No. 12/823,428, dated Nov. 15, 2010 (9 pages).

* cited by examiner

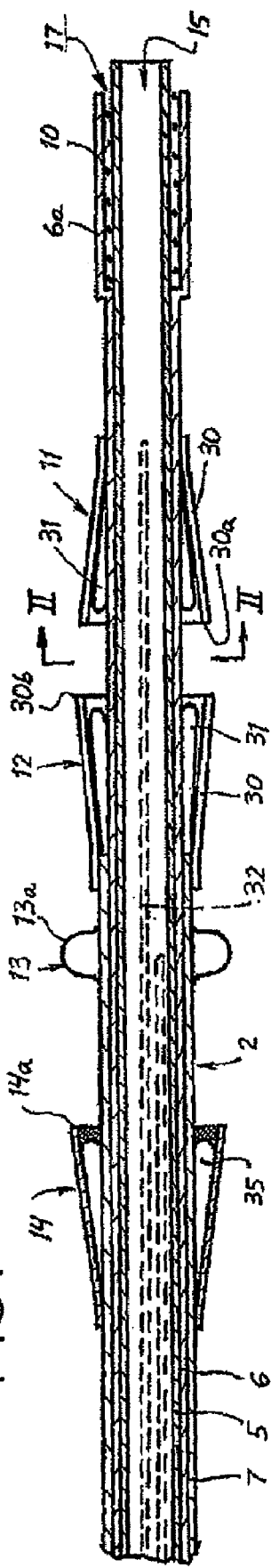
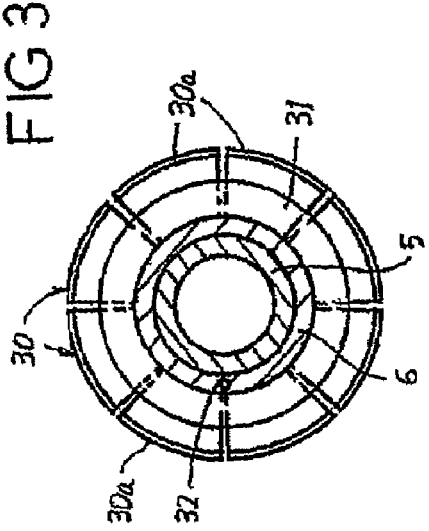
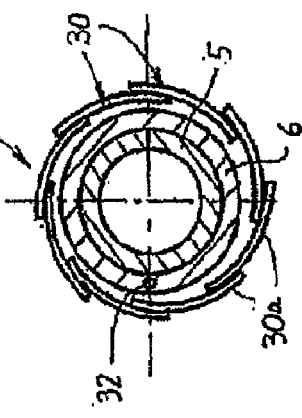

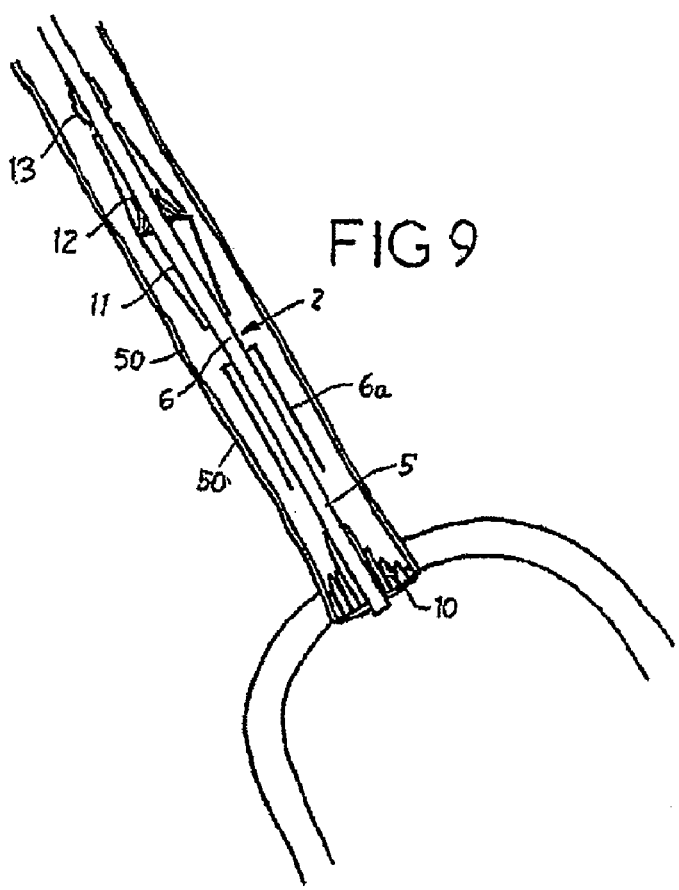
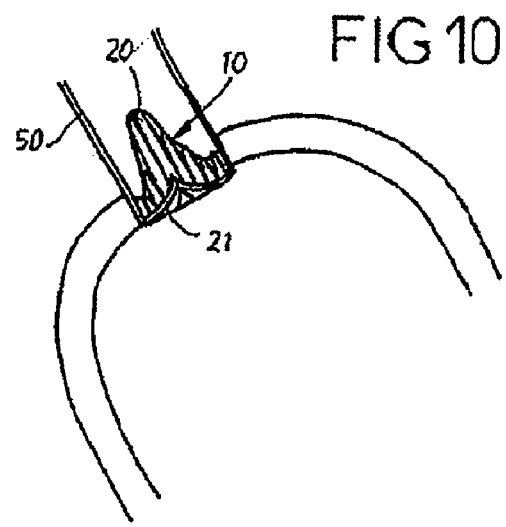
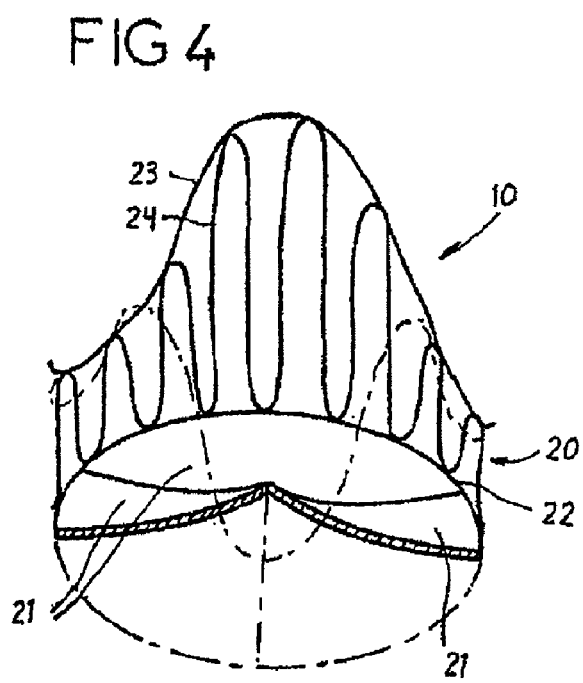

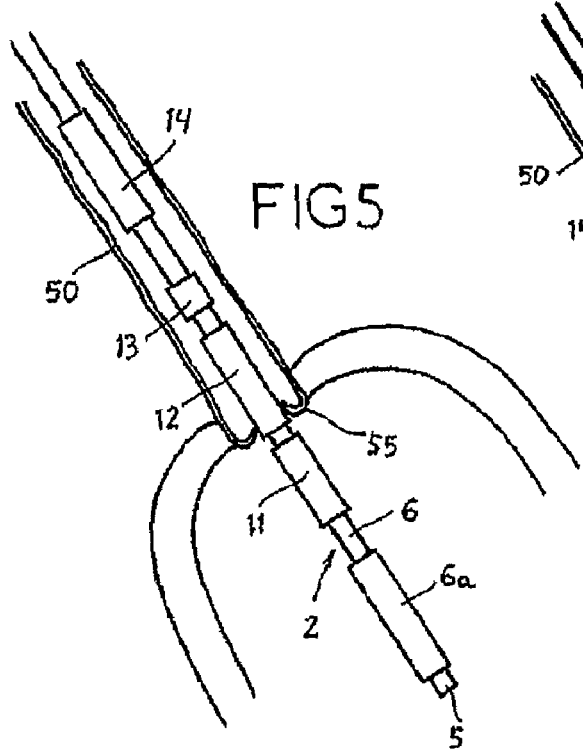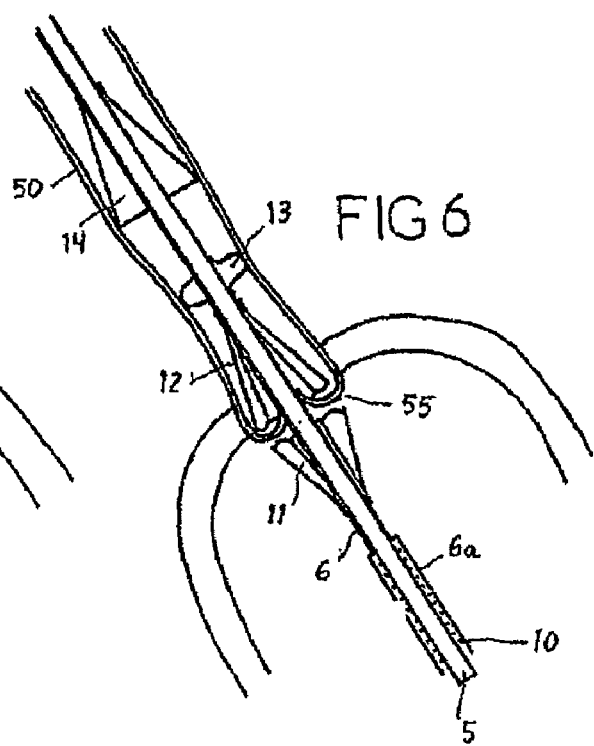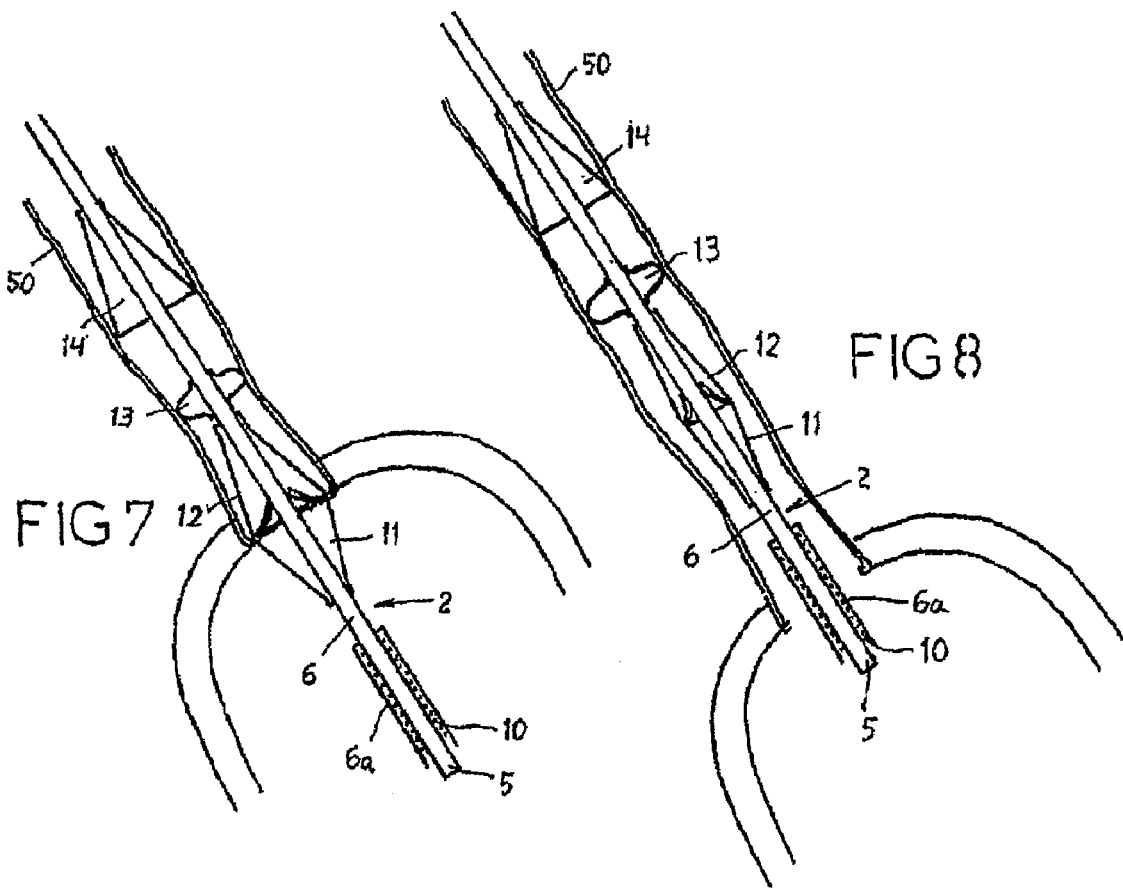

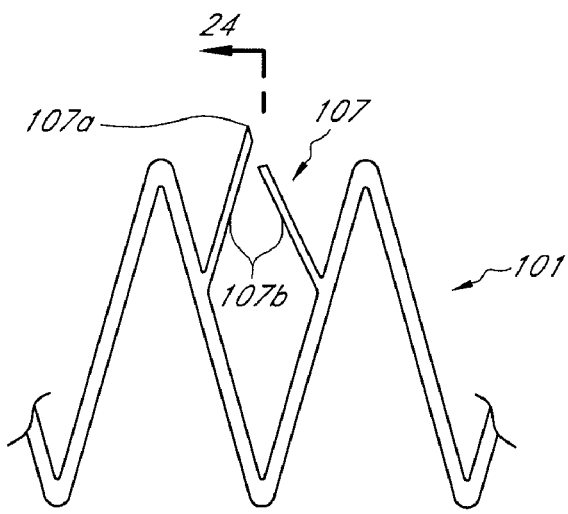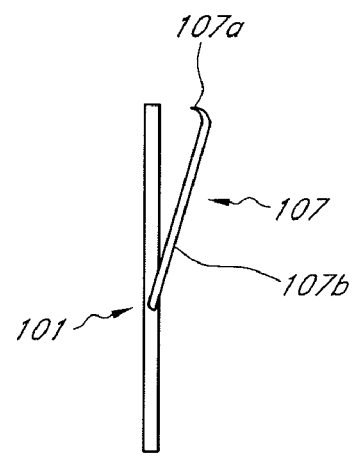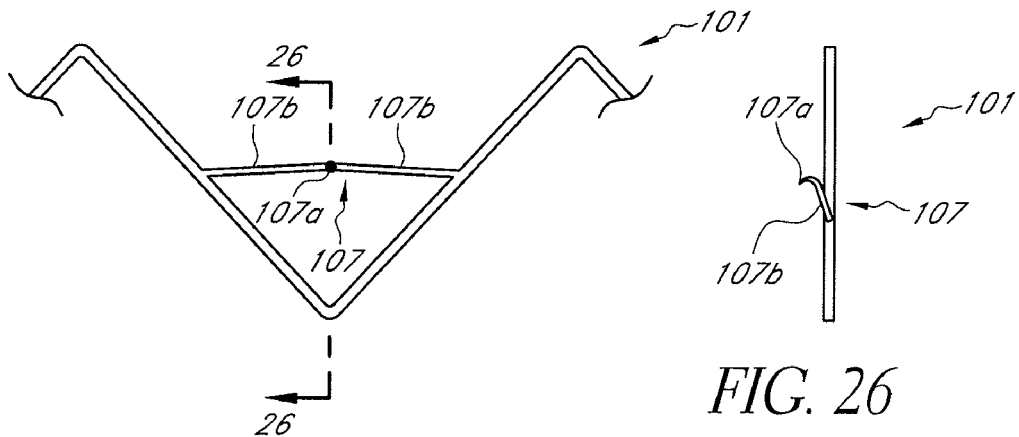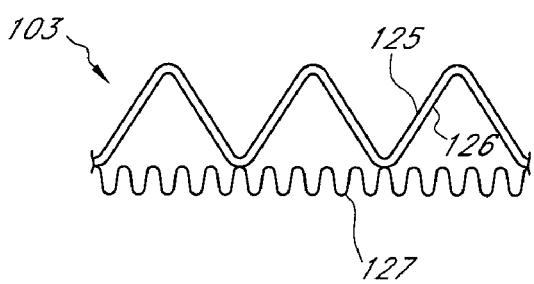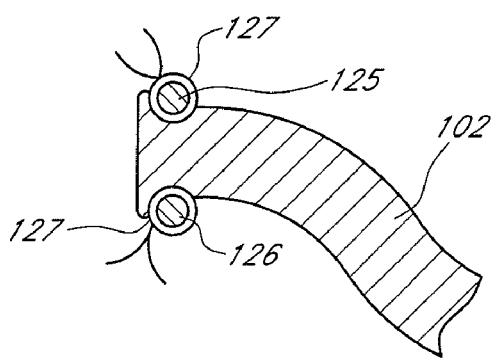
FIG. 23
FIG. 24
FIG. 25
FIG. 26
FIG. 27
FIG. 28

PROSTHETIC VALVE FOR TRANSLUMINAL DELIVERY

CROSS-REFERENCE TO RELATED APPLICATIONS

The present application claims priority under 35 U.S.C. §120 as a continuation of U.S. application Ser. No. 12/029,031, filed Feb. 11, 2008, which is a continuation of U.S. application Ser. No. 11/352,614 filed Feb. 13, 2006, now U.S. Pat. No. 7,329,278, which is a continuation of U.S. application Ser. No. 10/412,634 filed Apr. 10, 2003, now U.S. Pat. No. 7,018,406, which is a continuation-in-part of U.S. application Ser. No. 10/130,355, now U.S. Pat. No. 6,830,584, which has a 371(c) date of Nov. 26, 2002 and is the U.S. national phase under §371 of International Application No. PCT/FR00/03176, filed on Nov. 15, 2000, which was published in a language other than English and which claims priority from French Application No. 99/14462 filed on Nov. 17, 1999, now French Patent No. 2,800,984; application Ser. No. 10/412,634is also a continuation-in-part of International Application No. PCT/FR01/03258 filed on Oct. 19, 2001, which was published in a language other than English and which claims priority from French Application No. 00/14028 filed on Oct. 31, 2000, now French Patent No. 2,815,844. The present application also claims priority under 35 U.S.C. §120 as a continuation of U.S. application Ser. No. 11/434,506 filed May 15, 2006,which is a continuation-in-part of U.S. application Ser. No. 10/772,101 filed Feb. 4, 2004, which is a continuation-in-part of U.S. application Ser. No. 10/412,634 filed Apr. 10, 2003, now U.S. Pat. No. 7,018,406, which is a continuation-in-part of U.S. application Ser. No. 10/130,355, now U.S. Pat. No. 6,830,584, which has a 371(c) date of Nov. 26, 2002 and is the U.S. national phase under §371 of International Application No. PCT/FR00/03176, filed on Nov. 15, 2000, which was published in a language other than English and which claims priority from French Application No. 99/14462 filed on Nov. 17, 1999, now French Patent No. 2,800,984; application Ser. No. 10/412,634 is also a continuation-in-part of International Application No. PCT/FR01/03258 filed on Oct. 19, 2001, which was published in a language other than English and which claims priority from French Application No. 00/14028 filed Oct. 31, 2000, now French Patent No. 2,815,844.

FIELD OF THE INVENTION

The present invention relates to a prosthetic cardiac valve and related deployment system that can be delivered percutaneously through the vasculature, and a method for delivering same.

BACKGROUND OF THE INVENTION

Currently, the replacement of a deficient cardiac valve is often performed by opening the thorax, placing the patient under extracorporeal circulation, temporarily stopping the heart, surgically opening the heart, excising the deficient valve, and then implanting a prosthetic valve in its place. U.S. Pat. No. 4,106,129 to Carpentier describes a bioprosthetic heart valve with compliant orifice ring for surgical implantation. This procedure generally requires prolonged patient hospitalization, as well as extensive and often painful recovery. It also presents advanced complexities and significant costs.

To address the risks associated with open heart implantation, devices and methods for replacing a cardiac valve by a less invasive means have been contemplated. For example, French Patent Application No. 99 14462 illustrates a technique and a device for the ablation of a deficient heart valve by percutaneous route, with a peripheral valvular approach. International Application (PCT) Nos. WO 93/01768 and WO 97/28807, as well as U.S. Pat. Nos. 5,814,097 to Sterman et al., U.S. Pat. No. 5,370,685 to Stevens, and U.S. Pat. No. 5,545,214 to Stevens illustrate techniques that are not very invasive as well as instruments for implementation of these techniques.

U.S. Pat. No. 3,671,979 to Moulopoulos and U.S. Pat. No. 4,056,854 to Boretos describe a catheter mounted artificial heart valve for implantation in close proximity to a defective heart valve. Both of these prostheses are temporary in nature and require continued connection to the catheter for subsequent repositioning or removal of the valve prosthesis, or for subsequent valve activation.

With regard to the positioning of a replacement heart valve, attaching this valve on a support with a structure in the form of a wire or network of wires, currently called a stent, has been proposed. This stent support can be contracted radially in such a way that it can be introduced into the body of the patient percutaneously by means of a catheter, and it can be deployed so as to be radially expanded once it is positioned at the desired target site. U.S. Pat. No. 3,657,744 to Ersek discloses a cylindrical, stent-supported, tri-leaflet, tissue, heart valve that can be delivered through a portion of the vasculature using an elongate tool. The stent is mounted onto the expansion tool prior to delivery to the target location where the stent and valve is expanded into place. More recently, U.S. Pat. No. 5,411,552 to Andersen also illustrates a technique of this type. In the Andersen patent, a stent-supported tissue valve is deliverable percutaneously to the native heart valve site for deployment using a balloon or other expanding device. Efforts have been made to develop a stent supported valve that is self-expandable, using memory materials such as Nitinol.

The stent supported systems designed for the positioning of a heart valve introduce uncertainties of varying degree with regard to minimizing migration from the target valve site. A cardiac valve that is not adequately anchored in place to resist the forces of the constantly changing vessel wall diameter, and turbulent blood flow therethrough, may dislodge itself, or otherwise become ineffective. In particular, the known stents do not appear to be suited to sites in which the cardiac wall widens on either proximally and/or distally of the valve annulus situs. Furthermore, the native cardiac ring remaining after ablation of the native valve can hinder the positioning of these stents. These known systems also in certain cases create problems related to the sealing quality of the replacement valve. In effect, the existing cardiac ring can have a surface that is to varying degrees irregular and calcified, which not only lessens the quality of the support of the stent against this ring but also acts as the source of leaks between the valve and this ring. Also, these systems can no longer be moved at all after deployment of the support, even if their position is not optimal.

Also, the existing techniques are, however, considered not completely satisfactory and capable of being improved. In particular, some of these techniques have the problem of involving, in any case, putting the patient under extracorporeal circulation and temporarily stopping of the heart; they are difficult to put into practice; they do not allow precise control of the diameter according to which the natural valve is cut, in view of the later calibration of the prosthetic valve; they lead to risks of diffusion of natural valve fragments, often calcified, into the organism, which can lead to an embolism, as well as to risks of perforation of the aortic or cardiac wall; they, moreover, induce risks of acute reflux of blood during ablation of the natural valve and risks of obstruction of blood flow during implantation of the device with a balloon expandable stent for example.

SUMMARY OF THE INVENTION

The object of the present invention is to transluminally provide a prosthetic valve assembly that includes features for preventing substantial migration of the prosthetic valve assembly once delivered to a desired location within a body. The present invention aims to remedy these significant problems. Another objective of the invention is to provide a support at the time of positioning of the replacement valve that makes it possible to eliminate the problem caused by the native valve sheets, which are naturally calcified, thickened and indurated, or by the residues of the valve sheets after valve resection. Yet another objective of the invention is to provide a support making possible complete sealing of the replacement valve, even in case of an existing cardiac ring which has a surface which is to varying degrees irregular and/or to varying degrees calcified. Another objective of the invention is to have a device that can adapt itself to the local anatomy (i.e. varying diameters of the ring, the subannular zone, the sino-tubular junction) and maintain a known diameter of the valve prosthesis to optimize function and durability. The invention also has the objective of providing a support whose position can be adapted and/or corrected if necessary at the time of implantation.

The present invention is a prosthesis comprising a tissue valve supported on a self-expandable stent in the form of a wire or a plurality of wires that can be contracted radially in order to make possible the introduction of the support-valve assembly into the body of the patient by means of a catheter, and which can be deployed in order to allow this structure to engage the wall of the site where the valve is to be deployed. In one embodiment, the valve is supported entirely within a central, self-expandable, band. The prosthetic valve assembly also includes proximal and distal anchors. In one embodiment, the anchors comprise discrete self-expandable bands connected to the central band so that the entire assembly expands in unison into place to conform more naturally to the anatomy. The valve can be made from a biological material, such as an animal or human valve or tissue, or from a synthetic material, such as a polymer, and includes an annulus, leaflets, and commissure points. The valve is attached to the valve support band with, for example, a suture. The suture can be a biologically compatible thread, plastic, metal, or adhesive, such as cyanoacrylate.

In one embodiment, the valve support band is made from a single wire bent in a zigzag manner to form a cylinder. Alternatively, the valve support band can be made from a plurality of wires interwoven with one another. The wire can be made from stainless steel, silver, tantalum, gold, titanium, or any suitable tissue or biologically compatible plastic, such as ePTFE or Teflon. The valve support band may have a loop at its ends so that the valve support band can be attached to an upper anchor band at its upper end, and a lower anchor band at its lower end. The link can be made from, for example, stainless steel, silver, tantalum, gold, titanium, any suitable plastic material, or suture.

The prosthetic valve assembly is compressible about its center axis such that its diameter can be decreased from an expanded position to a compressed position. The prosthetic valve assembly may be loaded onto a catheter in its compressed position, and so held in place. Once loaded onto the catheter and secured in the compressed position, the prosthetic valve assembly can be transluminally delivered to a desired location within a body, such as a deficient valve within the heart. Once properly positioned within the body, the catheter can be manipulated to release the prosthetic valve assembly and expand it into its expanded position. In one embodiment, the catheter includes adjustment hooks such that the prosthetic valve assembly may be partially released and expanded within the body and moved or otherwise adjusted to a final desired location. At the final desired location, the prosthetic valve assembly may be totally released from the catheter and expanded to its full expanded position. Once the prosthetic valve assembly is totally released from the catheter and expanded, the catheter may be removed from the body.

Other embodiments are contemplated. In one such alternative embodiment, this structure comprises an axial valve support portion, which has a structure in the form of a wire or in the form of a network of wires suitable for receiving the replacement valve mounted on it, and suitable for supporting the cardiac ring remaining after the removal of the deficient native valve; at least one axial wedging portion, which has a structure in the form of a wire or in the form of a network of wires that is distinct from the structure of said axial valve support portion, and of which at least a part has, when deployed a diameter greater or smaller than that of said deployed axial valve support portion, such that this axial wedging portion is suitable for supporting the wall bordering said existing cardiac ring; and at least a wire for connecting said portions, this wire or these wires being connected at points to these portions in such a way as not to obstruct the deployment of said axial portions according to their respective diameters. The embodiment thus provides a support in the form of at least two axial portions that are individualized with respect to one another with regard to their structure, which are connected in a localized manner by at least one wire; where this wire or these wires do not obstruct the variable deployment of the axial portion with the valve and of the axial wedging portion(s).

The presence of a structure in the form of a wire or in the form of a network of wires in the axial valve support portion makes possible a perfect assembly of this valve with this structure, and the shape as well as the diameter of this axial portion can be adapted for supporting the existing cardiac ring under the best conditions. In particular, this axial valve support portion can have a radial force of expansion such that it pushes back ("impacts") the valve sheets that are naturally calcified or the residues of the valve sheets after valve resection onto or into the underlying tissues, so that these elements do not constitute a hindrance to the positioning of the replacement valve. This structure also makes it possible to support possible anchoring means for the support and/or possible sealing means for the space existing between the existing cardiac ring and the replacement valve, as indicated below.

The form and/or diameter of each axial wedging portion can be adapted for supporting the cardiac wall situated at the approach to the existing cardiac ring under the best conditions. In particular, this axial wedging portion can have a tubular shape with a constant diameter greater than that of the axial valve support portion, or the form of a truncated cone whose diameter increases with distance from the axial valve support portion.

Preferably, the tubular support has an axial valve support portion in the form of at least two parts, of which at least one is suitable for supporting the valve and of which at least another is suitable for pushing back the native valve sheets or the residues of the native valve sheets after valve resection, into or onto the adjacent tissue in order to make this region able to receive the tubular support. This axial valve support portion eliminates the problem generated by these valve or cardiac ring elements at the time of positioning of the replacement valve. The radial force of this axial valve support portion, by impacting all or part of the valvular tissue or in the wall or its vicinity in effect ensures a more regular surface more capable of receiving the valve support axis. It also ensures a better connection with the wall while reducing the risk of peri-prosthetic leakage. Furthermore, such a structure permits the valve to maintain a diameter within a preset range to ensure substantial coaptivity and avoid significant leakage.

Specifically, in order to support the valve, the axial valve support portion can have a part in the form of an undulating wire with large-amplitude undulations, and a part in the form of an undulating wire with small-amplitude undulations, adjacent to said part with large amplitude undulations, having a relatively great radial force in order to make it possible to push said valvular tissue against or into the wall of the passage. Preferably, the support according to one embodiment of the present invention has two axial wedging portions, one connected to an axial end of said valve support portion and the other to the other axial end of this same valve support portion. These two axial wedging portions thus make it possible to wedge the support on both sides of the existing cardiac ring, and consequently make possible complete wedging of the support in two opposite directions with respect to the treated site. If necessary, for example, in the case in which the passage with the valve has an aneurysm, the support according to the invention has: an axial holding portion, suitable for supporting in the deployed state the wall of the passage, and connecting wires such as the aforementioned connecting wires, connecting said axial valve support portion and said axial holding portion, these wires having a length such that the axial holding portion is situated after implantation a distance away from the axial valve support portion. This distance allows said axial holding portion to rest against a region of the wall of the passage not related to a possible defect which may be present at the approach to the valve, particularly an aneurysm. The length of the connecting wires can also be calculated in order to prevent the axial holding portion from coming into contact with the ostia of the coronary arteries. The aforementioned axial portions (valve support, wedging, holding portions) can have a structure in the form of an undulating wire, in zigzag form, or preferably a structure in diamond-shaped mesh form, the mesh parts being juxtaposed in the direction of the circumference of these portions. This last structure allows a suitable radial force making it possible to ensure complete resting of said portions against the wall which receives them.

The support according to the invention can be produced from a metal that can be plastically deformed. The instrument for positioning of the support then includes a balloon which has an axial portion with a predetermined diameter, adapted for realizing the deployment of said axial valve support portion, and at least one axial portion shaped so as to have, in the inflated state, a greater cross section than that of the passage to be treated, in such a way as to produce the expansion of the axial wedging portion placed on it until this axial wedging portion encounters the wall which it is intended to engage. The support according to this embodiment of the present invention can also be produced from a material that can be elastically deformed or even a material with shape memory, such as the nickel-titanium alloy of the type known as "Nitinol," which can be contracted radially at a temperature different from that of the body of the patient and which regains its original shape when its temperature approaches or reaches that of the body of the patient.

According to another possibility, the support is produced from a material with shape memory but that can be plastically deformed, or has parts made from a material with shape memory and parts made from a material that can be plastically deformed, and is formed in such a way that it can be brought, by shape memory or plastic deformation, from a state of contraction to a stable intermediate state of deployment between the state of contraction and the state of total deployment, and then by plastic deformation or shape memory respectively, from said intermediate state of deployment to said state of total deployment; in said intermediate state of deployment, the support has dimensions such that it remains mobile with respect to the site to be treated. The support is thus brought to the site to be treated and then is deployed from its intermediate state; its position can then possibly be adapted and/or corrected, and then the support is brought to its state of total deployment. Specifically, the aforementioned material may have shape memory but that can be plastically deformed, such as a nickel-titanium alloy of the type called "martensitic Nitinol" that can undergo plastic deformation by means of a balloon.

Advantageously, the support according to the invention has some anchoring means suitable for insertion into the wall of the site to be treated, and is shaped in such a way as to be mobile between an inactive position, in which it does not obstruct the introduction of the support into the body of the patient, and an active position, in which it is inserted into the wall of the site to be treated. Substantially complete immobilization of the support at the site is thus obtained. In particular, this anchoring means can be in the form of needles and can be mounted on the support between retracted positions and radially projected positions. Advantageously, the axial valve support portion has, at the site of its exterior surface, a sealing means shaped in such a way as to absorb the surface irregularities that might exist at or near the existing cardiac ring. This sealing means can consist of a peripheral shell made from a compressible material such as polyester or tissue identical to the valve or a peripheral shell delimiting a chamber and having a radially expandable structure, this chamber being capable of receiving an inflating fluid suitable for solidifying after a predetermined delay following the introduction into said chamber. This sealing means can also include a material that can be applied between the existing cardiac ring and the axial valve support portion, this material being capable of solidifying after a predetermined delay following this application. Specifically, in this case, this material is capable of heat activation, for example, by means of a laser, through the balloon, or capable of activation by emission of light of predetermined frequency, for example, by means of an ultraviolet laser, through the balloon. Said sealing means can also be present in the form of an inflatable insert with a spool-shaped cross section in the inflated state, which can be inserted between the existing cardiac ring and the axial valve support portion, Said spool shape allows this insert to conform to the best extent possible to the adjacent irregular structures and to provide a better seal.

An assembly and method for removing the native valve is also contemplated. In particular, the invention has the objective of providing a device which gives complete satisfaction with regard to the exeresis and replacement of the valve, while allowing one to operate without opening of the thorax, stopping of the heart and/or opening of the heart, and preventing any diffusion into the circulatory system of fragments of the removed valve. In one embodiment, the device comprises: an elongated support element; a first series of elongated blades arranged around the circumference of said elongated element; these blades are connected in a pivoting manner to the elongated element at the site of their proximal longitudinal ends and each has a sharp edge at the site of its distal longitudinal end; these blades can pivot with respect to the elongated element between a folded up position, in which they are near the wall of the elongated element in such a way that they do not stand in the way of the introduction and sliding of the device in the body channel in which the valve is located, in particular in the aorta, and an opened out position, in which these blades are spread out in the form of a corolla in such a way that their sharp edges are placed in extension of one another and thus constitute a sharp circular edge; a second series of blades, arranged consecutively to said first series of blades in the distal direction; the blades of this second series of blades have a structure identical to that of the blades of said first series of blades, except that these blades of this second series are connected to the elongated element by their distal longitudinal ends and each has a sharp edge at the site of its proximal longitudinal end; means making it possible to bring the blades of said first and second series of blades from their folded up position to their opened out position; means making it possible to move said series of blades axially in the direction of one another, between a position of mutual distancing of these series of blades, in which one series of blades can be placed axially on one side of the natural valve while the other series of blades is placed axially on the other side of this valve, and a close together position, in which the sharp circular edges of these two series of blades are brought in mutual contact and thus cut off the natural valve, making it possible to position each of the two aforementioned series of blades on one side of this valve.

The device according to the invention can be introduced percutaneously into said body channel and can be slid in this channel until each of the aforementioned series of blades is placed on one side of the valve. This position is identified using said means of identification. A system of peripheral perfusion or extracorporeal circulation or a blood pump through the center of the delivery system pumping blood from the left ventricle (proximal to the aortic valve) to the aorta (distal to the aortic valve) can be put in place in order to facilitate the flow of the blood, for the purpose of preventing stagnation of the blood in the heart. After the aforementioned positioning of the device, the blades of the two series of blades are spread out; then these two series are brought closer together until the valve is cut off. The configuration of these blades makes it possible to execute this cutting in a single operation, therefore without generating fragments which can be diffused into the circulatory system, or at the very least generating only very few such fragments; this configuration moreover makes possible precise control of the diameter according to which the natural valve is cut, in view of later calibration of the prosthetic valve. The blades are then brought back to the folded up position. The prosthetic valve is then put in place.

This valve can be separate from the device, in which case the latter is removed and then the prosthetic valve is introduced and positioned in said body channel by means of a separate device. Preferably however, the device according to the invention includes a proximal prosthetic valve, with a structure which can be spread out radially, with it possible for this prosthetic valve to occupy a folded up position, in which it is near the wall of said elongated element and does not sand in the way of the introduction and siding of the device in said body channel, and an opened out position, in which it rests against the wall of this channel and is capable of replacing the natural cardiac valve.

The device thus makes it possible to introduce and to position the prosthetic valve at the appropriate place in the body channel, by the same action as that making it possible to cut off the natural valve. After cutting off of the latter, the device is slid axially in the distal direction in order to bring the prosthetic valve to the appropriate site in this channel, after which this prosthetic valve is spread out. The device is then withdrawn, and the cut off natural valve is recovered.

Preferably, said elongated support element is a tubular catheter. This catheter thus allows the blood to flow through it during the exeresis of the natural valve. The cross section of the channel of this catheter can be sufficient to allow the blood to flow through this channel with or without the help of a pump, which limits or prevents resorting to putting the patient in extracorporeal circulation. The catheter can also have a small diameter, which facilitates the introduction and sliding of the device in the body channel, but it is then necessary to provide peripheral circulation by an external assistance system such as an extracorporeal circulation system. The catheter has a lateral distal opening in order to allow the blood to rejoin the body channel, for example, the ascending aorta, this opening being arranged in such a way that the length of catheter passed through the blood is as short as possible.

Preferably, the device has a distal inflatable balloon, placed at the site of the exterior surface of said elongated element; this balloon is configured so as to occupy a folded up position, in which it has a cross section such that it does not stand in the way of the introduction and to the sliding of the device in said body channel, and an opened out position, in which it occupies he whole space existing between the exterior surface of said elongated element and the wall of said body channel and rests, by a peripheral edge which it has, against this wall. The balloon is inflated after the positioning of the series of blades on both sides of the natural valve, in order to prevent reflux of the blood during the ablation of the natural valve. If said elongated element is a catheter, this balloon moreover makes it possible to case this blood to flow only through the catheter. Once the prosthetic valve is positioned, the balloon is brought back to a folded up position so as to re-establish the blood flow through the body channel.

Preferably, the device has a distal filter made of flexible material, placed in the site of the exterior surface of said elongated element; this filter is configured so that it can occupy a folded up position, in which it has a cross section such that it does not stand in the way of the introduction and sliding of the device in said body channel, and an opened out position, in which it occupies the whole space existing between the exterior surface of said elongated element and the wall of the channel and rests, by a peripheral edge which it has, against this wall. This filter makes it possible to catch possible fragments generated by the exeresis of the valve and to retain them so that they are removed from the blood circulation. The device can have some means making it possible to move said series of blades in the axial direction independently from said balloon and/or from said filter. Once opened out, this or these means do not have to be moved axially in the body channel during the aforementioned axial movement of the series of blades.

Said balloon and/or said filter can also be separate from the device, being mounted on an elongated support element which belongs to them. In case of operation on a mitral valve, this balloon and/or this filter is/are introduced into the aorta by a peripheral artery route, and the device is itself introduced into the heart by the peripheral venous system, up to the right atrium and then into the left atrium through the interatrial septum, up to the site of the mitral valve. The prosthetic valve can advantageously have a frame made of a material with a shape memory, particularly a nickel-titanium alloy known as "Nitinol." This same valve can have valves made of biological material (preserved animal or human valves) or valves made of synthetic material such as a polymer. When replacing an aortic valve the device may be alternatively introduced in a retrograde manner through a peripheral artery (femoral artery) or through a venous approach and trans-septally (antegrade).

The above embodiments and methods of use are explained in more detail below.

BRIEF DESCRIPTION OF THE DRAWINGS

FIG. 1 is a cross-sectional side view of one embodiment of an assembly of the present invention for removing and replacing a native heart valve percutaneously;

FIG. 2 is a cross-section axial view of the assembly of FIG. 1 taken at line II-II, shown in a closed condition;

FIG. 3 is a cross-section axial view of the assembly of FIG. 1 taken at line II-II, shown in an opened condition;

FIG. 4 is a perspective schematic view of one embodiment of a prosthetic valve of the present invention;

FIGS. 5 to 9 are schematic views of the assembly of the present invention positioned in a heart, at the site of the valve that is to be treated, during the various successive operations by means of which this valve is cut out and the prosthetic valve shown in FIG. 4 deployed;

FIG. 10 is a schematic view of the prosthetic valve shown of FIG. 4 shown in a deployed state;

FIG. 23 is a detail view of the support of FIG. 22 shown in the contracted state;

FIG. 24 is a detail view of the support of FIG. 23 taken along line 23-23;

FIG. 25 is a detail view of the support of FIG. 22 shown in the expanded state;

FIG. 26 is a detail view of the support of FIG. 25 taken along line 25-25;

FIG. 27 is a schematic view of an alternative embodiment of the present invention;

FIG. 28 is a detailed cross section view of the support of FIG. 27;

DETAILED DESCRIPTION OF THE PREFERRED EMBODIMENT

Figure 11:
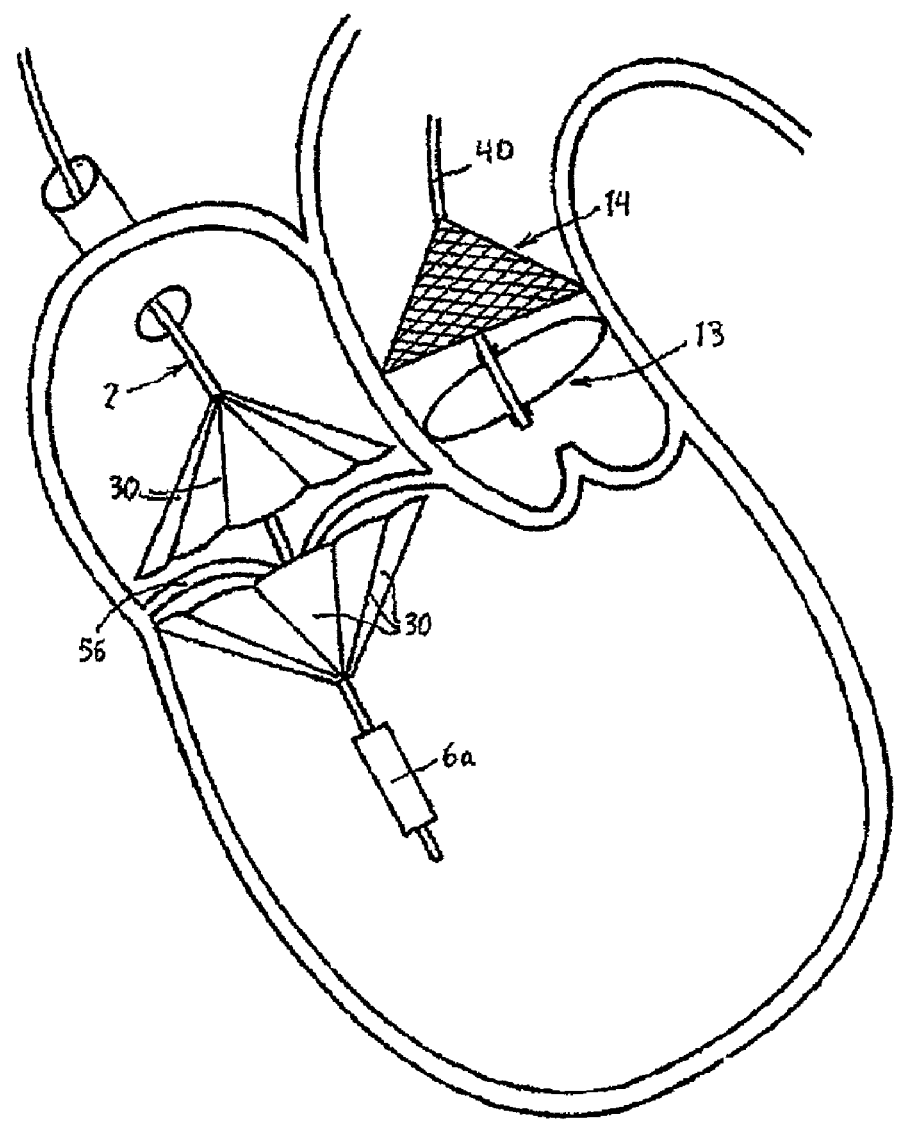
FIG. 11 is a schematic view of an alternative embodiment of the assembly of the present invention shown treating a mitral valve.

Reference is now made to the figures wherein like parts are designated with like numerals throughout. FIGS. 1 to 3 represent a device 1 for replacing a heart valve by a percutaneous route. This device comprises a tubular catheter 2 formed from three tubes 5, 6, 7 engaged one inside the other and on which there are placed, from the proximal end to the distal end (considered with respect to the flow of blood, that is to say from right to left in FIG. 1), a prosthetic valve 10, two series of blades 11, 12, a balloon 13 and a filter 14. The three tubes 5, 6, 7 are mounted so that they can slide one inside the other. The interior tube 5 delimits a passage 15, the cross section of which is large enough to allow blood to flow through it. At the proximal end, the intermediate tube 6 forms a bell housing 6a delimiting, with the interior tube 5, an annular cavity 17 in which the prosthetic valve 10 is contained in the furled condition.

FIG. 4 shows that this valve 10 comprises an armature 20 and valve leaflets 21 mounted so that they are functionally mobile on this armature 20. The armature consists of a collection of wires 22, 23, 24 made of shape memory material, particularly of nickel-titanium alloy known by the name of "NITINOL;" namely, (i) a proximal end wire 22 which, when the valve 10 is in the deployed state, has a roughly circular shape; (ii) a distal end wire 23 forming three corrugations in the axial direction, these corrugations being distributed uniformly around the circumference of the valve 10, and (iii) an intermediate wire 24 forming longitudinal corrugations between the wires 22 and 23, this wire 24 being connected to the latter ones via the ends of each of these corrugations. The valve leaflets 21 for their part are made of biological material (preserved human or animal valve leaflets) or of synthetic material, such as a polymer. The armature 20 may, when its material is cooled, be radially contracted so that the valve 10 can enter the cavity 17. When this material is heated to body temperature, this armature 20 returns to its original shape, depicted in FIG. 4, in which it has a diameter matched to that of a bodily vessel, particularly the aorta, in which the native valve that is to be treated lies. This diameter of the armature 20 is such that the valve 10 bears against the wall of the bodily vessel and is immobilized in the axial direction with respect to that vessel.

Each series of blades 11, 12 comprises metal elongate blades 30 and an inflatable balloon 31 situated between the catheter 2 and these blades 30. The blades 30 have a curved profile and are arranged on the circumference of the catheter 2, as shown in FIGS. 2 and 3. The blades 30 of the proximal series 11 are connected pivotably to the tube 6 by their proximal ends and comprise a cutting distal edge 30a, while the blades 30 of the distal series 12 are connected pivotably to the exterior tube 7 by their distal ends and comprise a cutting proximal edge 30b. The connection between the blades 30 and the respective tubes 6 and 7 is achieved by welding the ends of the blades 30 together to form a ring, this ring being fixed axially to the corresponding tube 6, 7 by crimping this ring onto this tube 6, 7, the pivoting of the blades 30 being achieved by simple elastic deformation of these blades 30. This pivoting can take place between a position in which the blades 30 are furled, radially internally with respect to the catheter 2 and shown in FIGS. 1 and 2, and a position in which these blades 30 are unfurled, radially externally with respect to this catheter 2 and shown in FIG. 3. In the furled position, the blades 30 lie close to the wall of the tube 6 and partially overlap each other so that they do not impede the introduction and the sliding of the device 1 into and in the bodily vessel in which the native valve that is to be treated lies; in said unfurled position, the blades 30 are deployed in a corolla so that their cutting edges 30a, 30b are placed in the continuation of one another and thus constitute a circular cutting edge visible in FIG. 3.

Each balloon 31, placed between the tube 3 and the blades 30, may be inflated from the end of the catheter 2 which emerges from the patient, via a passage 32 formed in the tube 6. It thus, when inflated, allows the blades 30 to be brought from their furled position into their unfurled position, and performs the reverse effect when deflated. The axial sliding of the tube 6 with respect to the tube 7 allows the series of blades 11, 12 to be moved axially toward one another, between a spaced-apart position shown in FIG. 1, and a close-together position. In the former of these positions, one series of blades 11 may be placed axially on one side of the native valve while the other series of blades 12 is placed axially on the other side of this valve, whereas in the latter of these positions, the circular cutting edges of these two series of blades 11, 12 are brought into mutual contact and thus cut through the native valve in such a way as to detach it from said bodily vessel. The tubes 5 to 7 further comprise marks (not visible in the figures) in barium sulfate allowing the axial position of the device 1 with respect to the native valve to be identified percutaneously so that each of the two series of blades 11, 12 can be placed on one axial side of this valve. These tubes 5 to 7 also comprise lateral distal openings (not depicted) to allow the blood to reach the bodily vessel, these openings being formed in such a way that the length of catheter 2 through which the blood flows is as short as possible, that is to say immediately after the filter 14, in the distal direction.

The balloon 13 is placed on the exterior face of the tube 7, distally with respect to the series 12. This balloon 13 has an annular shape and is shaped to be able to occupy a furled position in which it has a cross section such that it does not impede the introduction and sliding of the device 1 into and in said bodily vessel, and an unfurled position, in which it occupies all of the space between the exterior face of the tube 7 and the wall of said bodily vessel and, via a peripheral edge 13a which it comprises, bears against this wall.

The filter 14 is placed distally with respect to the balloon 13, on the tube 7, to which it is axially fixed. This filter 14 is made of flexible material, for example polyester netting, and is shaped to be able to occupy a furled position in which it has a cross section such that it does not impede the introduction and sliding of the device 1 into and in said bodily vessel, and an unfurled position in which it occupies all of the space between the exterior face of the catheter 2 and the wall of this vessel and, via a peripheral edge 14a which it comprises, bears against this wall.

An inflatable balloon 35 is placed between the tube 7 and the filter 14 so as, depending on whether it is inflated or deflated, to bring the filter 14 into its respective unfurled and furled positions. In practice, as shown by FIGS. 5 to 9, the device 1 is introduced into said bodily vessel 50 by a percutaneous route and is slid along inside this vessel 50 until each of the series 11, 12 of blades is placed on one side of the native valve 55 that is to be treated (FIG. 5). This position is identified using the aforementioned marks. When the device is in this position, the proximal part of the catheter 2 is situated in the heart, preferably in the left ventricle, while the aforementioned distal lateral openings are placed in a peripheral arterial vessel, preferably in the ascending aorta. The balloons 13 and 35 are inflated in such a way as to cause blood to flow only through the passage 15 and prevent blood reflux during the ablation of the valve 55. A peripheral perfusion system is set in place to facilitate this flow. The blades 30 of the two series 11, 12 are then deployed (FIG. 6) by inflating the balloons 31, then these two series 11, 12 are moved closer together by sliding the tube 6 with respect to the tube 7, until the valve 55 is cut through (FIG. 7). The blades 30 are then returned to their furled position by deflating the balloons 31 while at the same time remaining in their close-together position, which allows the cut-out valve 55 to be held between them. The device 1 is then slid axially in the distal direction so as to bring the bell housing 6a to the appropriate position in the vessel 50 (FIG. 8), after which the valve 10 is deployed by sliding the tube 6 with respect to the tube 5 (FIG. 9). The balloons 13 and 35 are deflated then the device 1 is withdrawn and the cut-out valve 55 is recovered (FIG. 10).

FIG. 11 shows a second embodiment of the device 1, allowing operation on a mitral valve 56. The same reference numerals are used to denote the same elements or parts as the aforementioned, as long as these elements or parts are identical or similar in both embodiments. In this case, the tubular catheter is replaced by a support wire 2, on which one of the series of blades is mounted and by a tube engaged over and able to slide along this wire, on which tube the other series of blades is mounted; the passages for inflating the balloons 31 run along this support wire and this tube; the balloon 13 and the filter 14 are separate from the device 1 and are introduced into the aorta via a peripheral arterial route, by means of a support wire 40 along which the passages for inflating the balloons 13 and 35 run. The device 1, devoid of balloon 13 and the filter 14, is for its part introduced into the heart through the peripheral venous system, as far as the right atrium then into the left atrium through the inter-auricular septum, as far as the valve 56. For the remainder, the device 1 operates in the same way as was mentioned earlier. The invention thus provides a device for replacing a heart valve by a percutaneous route, making it possible to overcome the drawbacks of the prior techniques. Indeed the device 1 is entirely satisfactory as regards the cutting-away of the valve 55, 56, making it possible to operate without stopping the heart and making it possible, by virtue of the filter 14, to prevent any dispersion of valve fragments 55, 56 into the circulatory system.

Figure 12:
FIG. 12 is a cross-sectional view of a section of a blade used in excising the native valve.
Figure 13:
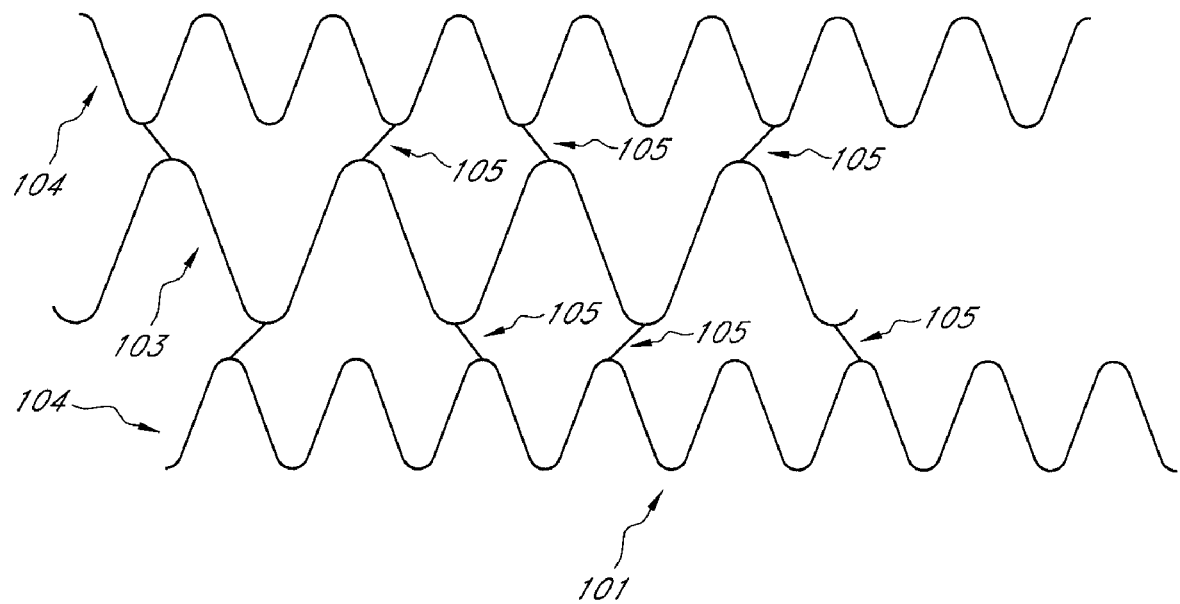
FIG. 13 is a schematic view of one embodiment of the support structure of the prosthesis assembly of the present invention.
Figure 14:
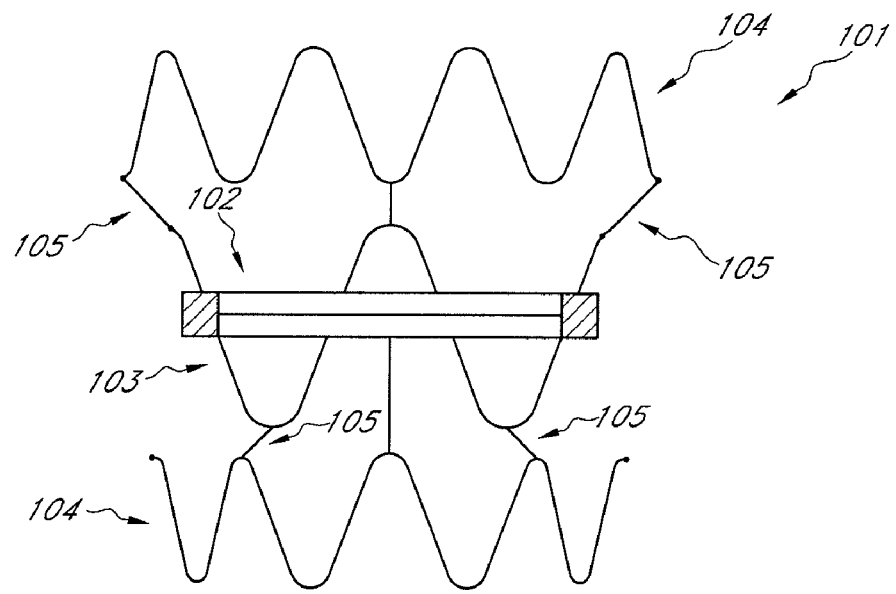
FIG. 14 is a cross-sectional view of the support of FIG. 13 showing a heart valve supported by the central portion of the support.
Figure 15:
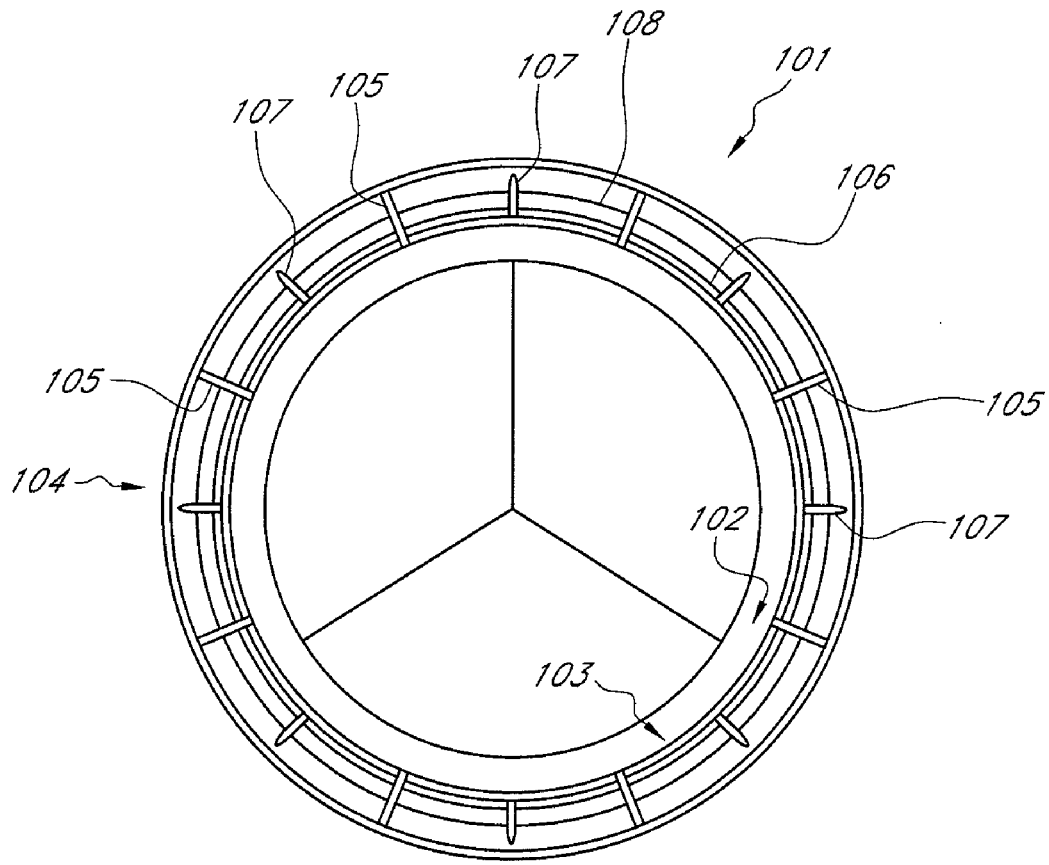
FIG. 15 is an end view of the support of FIGS. 13 and 14 in the deployed state.

The above device may comprise a fourth tube, engaged on and able to slide along the tube 7, this fourth tube comprising the balloon and the filter mounted on it and allowing said series of blades to be moved in the axial direction independently of said balloon and/or of said filter; the blades may be straight as depicted in the drawing or may be curved toward the axis of the device at their end which has the cutting edge, so as to eliminate any risk of lesion in the wall of the bodily vessel, as shown in FIG. 12; the filter 14 may be of the self-expanding type and normally kept in the contracted position by a sliding tube, which covers it, making the balloon 35 unnecessary.

FIGS. 13 to 16 represent tubular support 101 for positioning, by percutaneous route, of replacement heart valve 102. The support structure 101 includes median portion 103, which contains valve 102, two extreme wedging portions 104 and wires 105 for connecting these portions 103 and 104, Median portion 103 also includes peripheral shell 106 provided with anchoring needles 107 and shell 108 made of compressible material. As is particularly apparent from FIG. 13, each of portions 103 and 104 is formed with an undulating wire, and wires 105 connect pointwise the ends of the undulations of portion 103 to the end of an adjacent wave of portion 104. Portions 104, seen in expanded form, have lengths greater than the length of portion 103, so that when the ends of the wires respectively forming portions 103 and 104 are connected in order to form the tubular support structure 101, the diameter of portion 103 is smaller than the diameter of portions 104.

Figure 16:
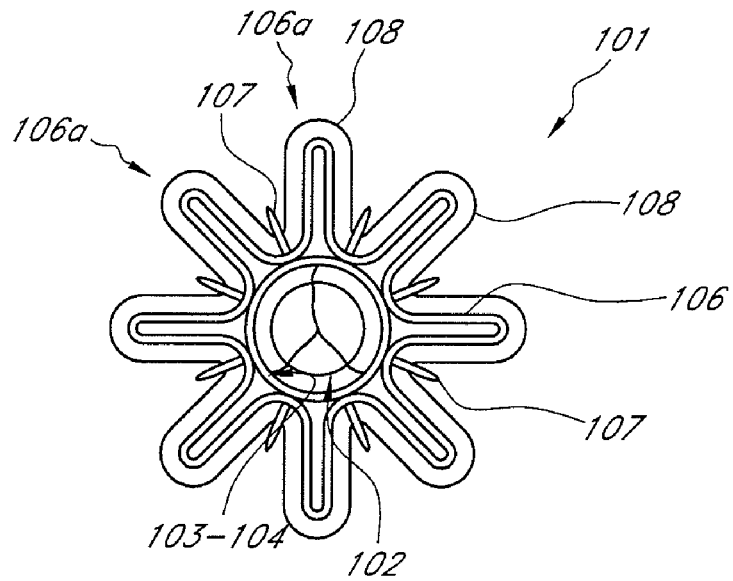
FIG. 16 is an end view of the support of FIGS. 13 and 14 in the contracted state.
Figure 17:
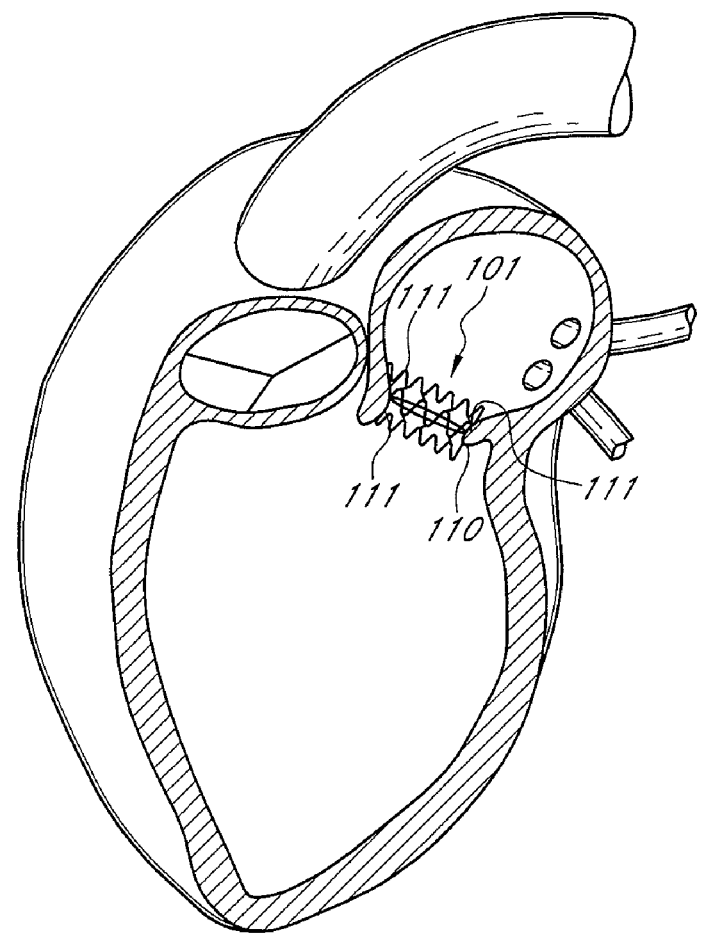
FIG. 17 is a schematic view of a heart with an embodiment of the present inventive prosthesis shown deployed in place.

The diameter of portion 103 is such that portion 103 can, as shown by FIG. 17, support cardiac ring 110 that remains after removal of the deficient native valve, while portions 104 cart support walls 111 bordering ring 110. These respective diameters are preferably such that said supporting operations take place with slight radial restraint of ring 110 and walls 111. Portion 103 presents in the deployed state a constant diameter. Portions 104 can have a constant diameter in the form of a truncated cone whose diameter increases away from portion 103. The entire support structure 101 can be made from a material with shape memory, such as the nickel-titanium alloy known as "Nitinol." This material allows the structure to be contracted radially, as shown in FIG. 16, at a temperature different form that of the body of the patient and to regain the original shape shown in FIGS. 14 and 15 when its temperature approaches or reaches that of the body of the patient. The entire support structure 101 can also be made from a material that can be expanded using a balloon, such as from medical stainless steel (steel 316 L). Valve 102 can be made of biological or synthetic tissue. It is connected to portion 103 by sutures or by any other appropriate means of attachment. It can also be molded on portion 103. Shell 106 may be made of "Nitinol." It is connected to the undulations of portion 103 at mid-amplitude, and has needles 107 at the site of its regions connected to these undulations. Needles 107 consist of strands of metallic wire pointed at their free ends, which project radially towards the exterior of shell 106.

This shell can take on the undulating form which can be seen in FIG. 16 in the contracted state of support 101 and the circular form which can be seen in FIG. 4 in the deployed state of this support 101. In its undulating form, shell 106 forms undulations 106a projecting radially on the outside of support 101, beyond needles 107, so that these needles 107, in the retracted position, do not obstruct the introduction of support 101 in a catheter or, once support 101 has been introduced into the heart using this catheter, do not obstruct the deployment out of this support 1. The return of shell 6 to its circular form brings needles 107 to a position of deployment, allowing them to be inserted in ring 110 in order to complete the anchoring of support 101. Shell 108 is attached on shell 106. Its compressible material allows it to absorb the surface irregularities which might exist at or near ring 110 and thus to ensure complete sealing of valve 102.

Figure 18:
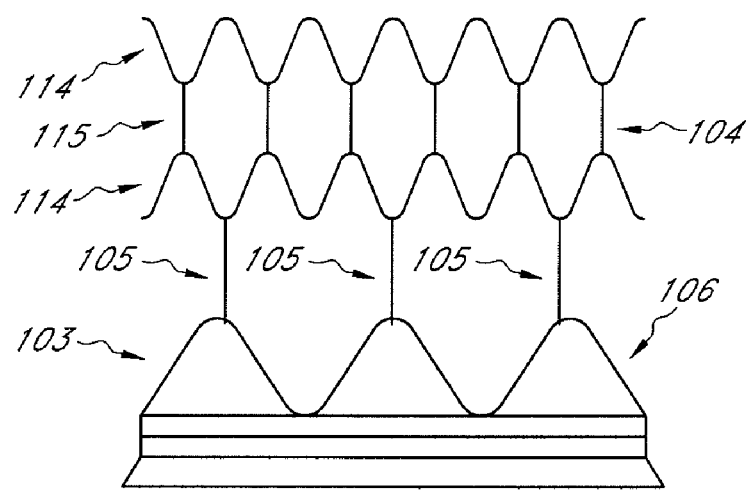
FIG. 18 is a schematic view of an alternative embodiment of the present invention.
Figure 19:
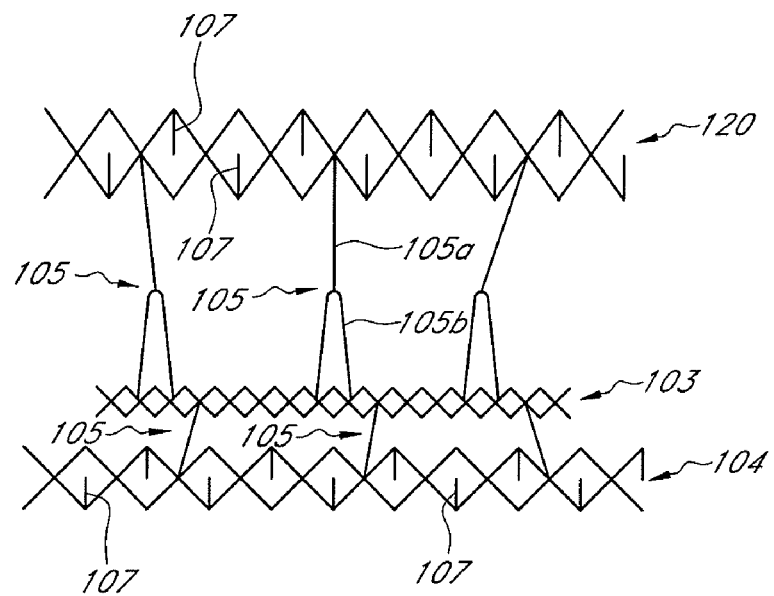
FIG. 19 is schematic view of an alternative embodiment of the present invention.

FIG. 18 shows a support structure 101 having a single portion 104 connected to portion 103 by wires 105. This portion 104 is formed by two undulating wires 114 connected together by wires 115. FIG. 19 shows a support structure 101 which has portion 103 and portion 104 connected by connecting wires 105. These portions 103 and 104 have diamond-shaped mesh structures, these mesh parts being juxtaposed in the direction of the circumference of these portions and connected together at the site of two of their opposite angles in the direction of the circumference of these portions 103 and 104. Wires 105 are connected to these structures at the site of the region of junction of two consecutive mesh parts. These mesh parts also have anchoring hooks 107 extending through them from one of their angles situated in the longitudinal direction of support 101.

Figure 20:
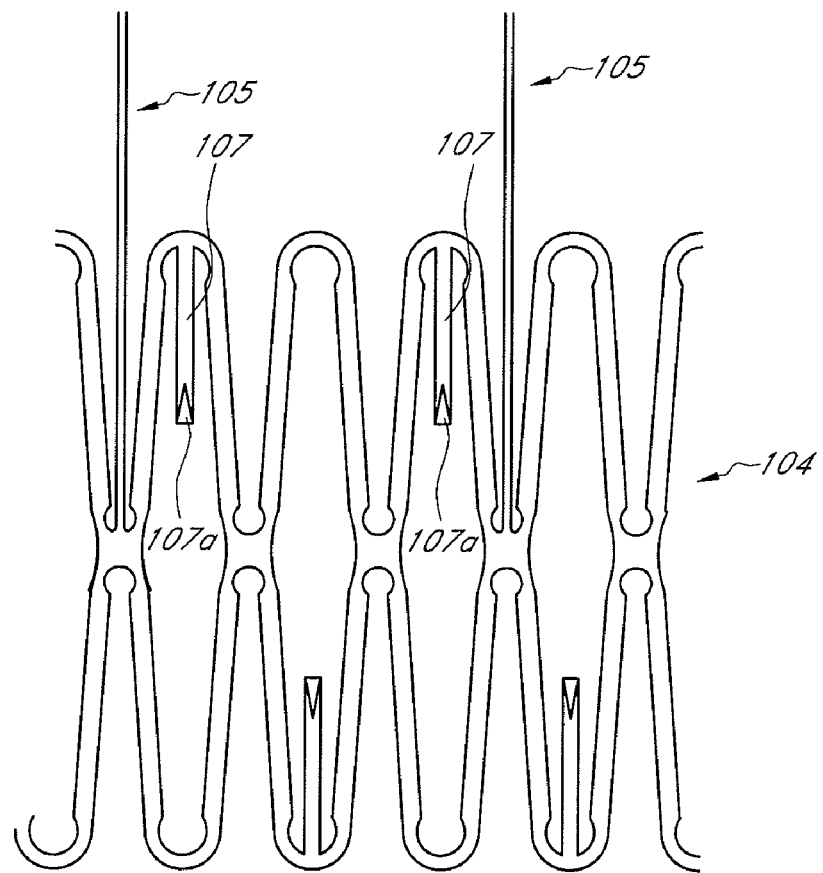
FIG. 20 is a detail view of a part of the support structure of one embodiment of the present invention.

FIG. 20 illustrates, in an enlarged scale, the structure of this portion 104 and of a part of wires 105, as cut, for example, with a laser from a cylinder of stainless steel, and after bending of sharp ends 107a of hooks 107. These hooks, in a profile view, can have the shape as shown in FIG. 4 or 26. The structure represented in FIG. 19 also has axial holding portion 120, which has a structure identical to that of portion 104 but with a coarser mesh size, and three wires 105 of significant length connecting this portion 120 to portion 103. These wires 105, on the side of portion 120, have a single link 105a and on the side of portion 103, a double link 105b. Their number corresponds to the three junctions formed by the three valves of valve 102, which facilitates mounting of valve 102 on support 101 thus formed. The support according to FIG. 19 is intended to be used, as appears in FIG. 21, when the body passage with the valve to be replaced, in particular the aorta, has a variation in diameter at the approach to the valve. The length of wires 105 connecting portions 103 and 120 is provided so that after implantation, portion 120 is situated in a non-dilated region of said body passage, and this portion 120 is provided so as to engage the wall of the passage.

Figure 22:
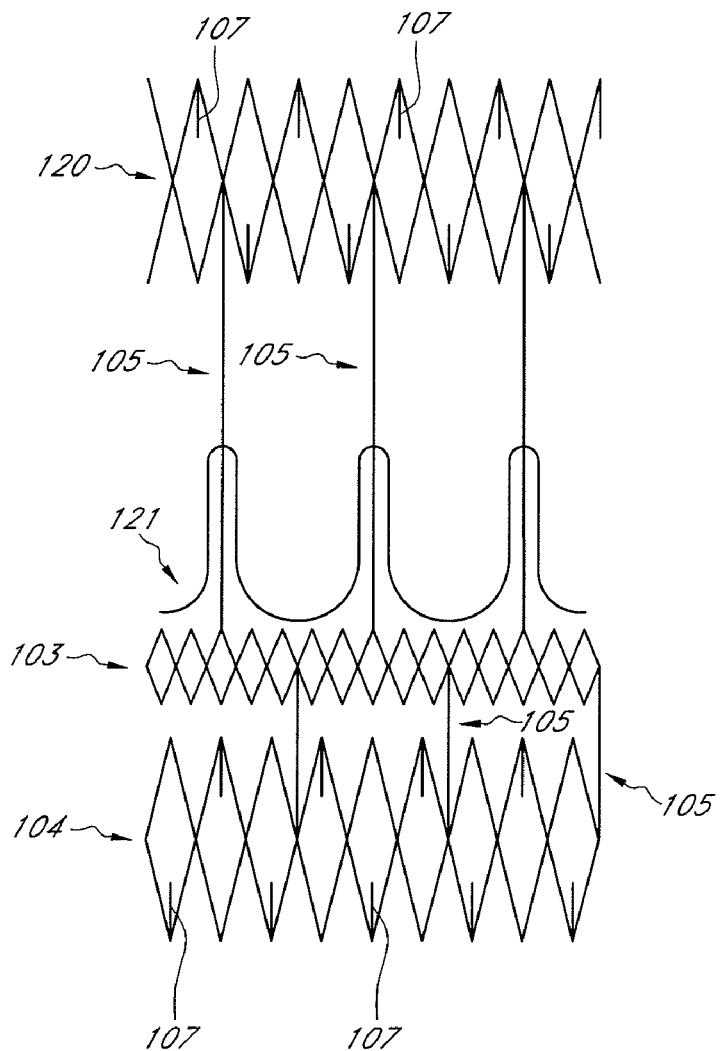
FIG. 22 is schematic view of an alternative embodiment of the present invention.

FIG. 22 shows a structure similar to that of FIG. 19 but unexpanded, except that the three wires 105 have a single wire structure but have an undulating wire 121 ensuring additional support near portion 103. This wire 121 is designed to support valve 102 with three valve leaflets. FIGS. 23 to 26 show an embodiment variant of the structure of portions 103, 104 or 120, when this structure is equipped with hooks 107. In this case, the structure has a zigzagged form, and each hook 107 has two arms 107b; each of these arms 107b is connected to the other arm 107b at one end and to an arm of structure 101 at its other end. The region of junction of the two arms 107b has bent hooking pin 107a.

Figure 29:
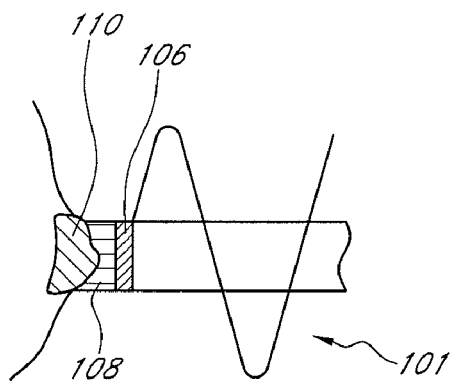
FIG. 29 is a partial schematic view in longitudinal section of the support of the present invention and of a calcified cardiac ring.
Figure 30:
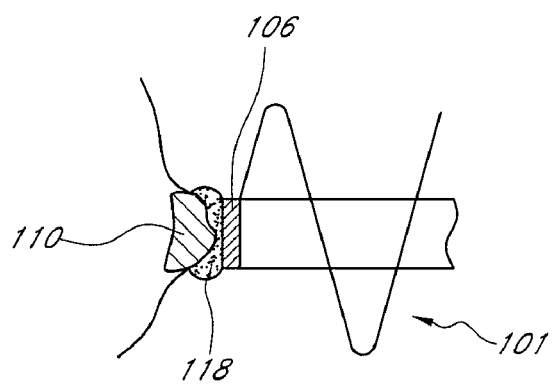
FIG. 30 is a schematic view of an alternative to the support of FIG. 29.

FIG. 27 shows portion 103 which has two undulating wires 125, 126 extending in the vicinity of one another and secondary undulating wire 127. As represented in FIG. 28, wires 125, 126 can be used to execute the insertion of valve 102 made of biological material between them and the attachment of this valve 102 to them by means of sutures 127. FIG. 29 shows a part of support 101 according to FIGS. 13 to 17 and the way in which the compressible material constituting shell 108 can absorb the surface irregularities possibly existing at or near ring 110, which result from calcifications. FIG. 30 shows support 101 whose shell 106 has no compressible shell. A material can then be applied, by means of an appropriate cannula (not represented), between ring 110 and this shell 106, this material being able to solidify after a predetermined delay following application.

Figure 31:
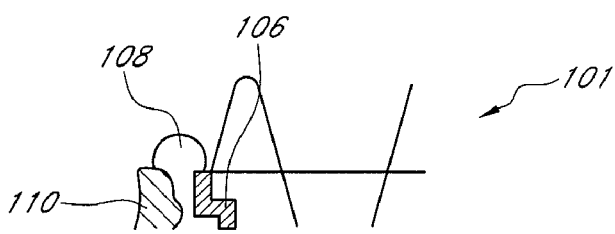
FIG. 31 is a schematic view of an alternative to the support of FIG. 29.

FIG. 31 shows support 101 whose shell 106 has a cross section in the form of a broken line, delimiting, on the exterior radial side, a lower shoulder. Housed in the step formed by this shoulder and the adjacent circumferential wall is peripheral shell 108 which can be inflated by means of a catheter (not represented). This shell 108 delimits a chamber and has a radially expandable structure, such that it has in cross section, in the inflated state, two widened ends projecting on both sides of shell 106. This chamber can receive an inflating fluid that can solidify in a predetermined delay following its introduction into said chamber. Once this material has solidified, the inflating catheter is cut off.

Figure 32:
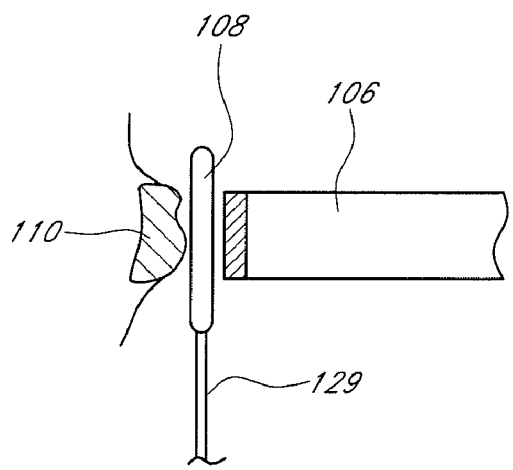
FIGS. 32 and 33 are schematic views of an alternative to the support of FIG. 29.
Figure 33:
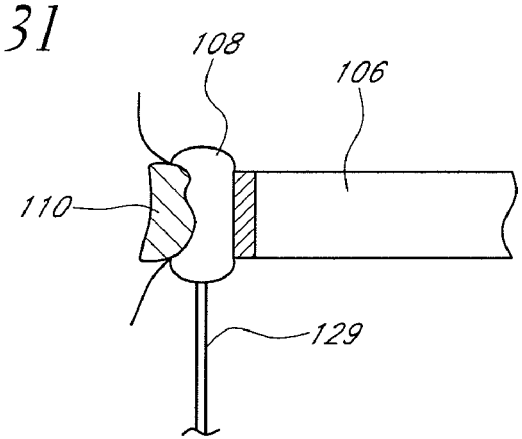

FIGS. 32 and 33 show support 101 whose shell 106 receives inflatable insert 108 which has a spool-shaped cross section in the inflated state; this insert 108 can be inflated by means of catheter 129. Insert 108 is positioned in the uninflated state (FIG. 32) at the sites in which a space exists between shell 106 and existing cardiac ring 110. Its spool shape allows this insert (cf. FIG. 33) to conform as much as possible to the adjacent irregular structures and to ensure a better seal.

Figure 21:
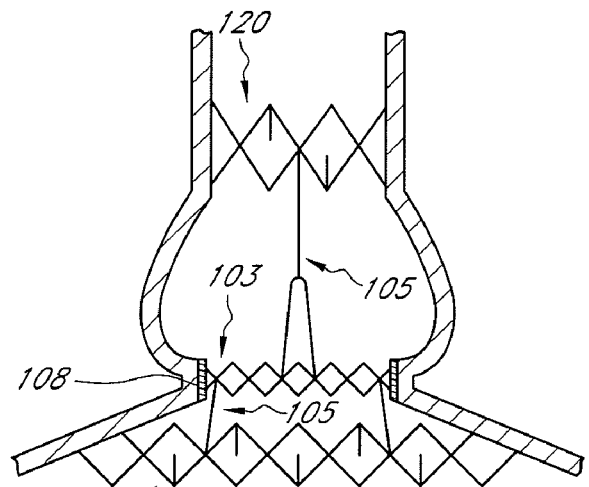
FIG. 21 is a schematic view of the support of FIG. 19 shown in a deployed state.
Figure 34:
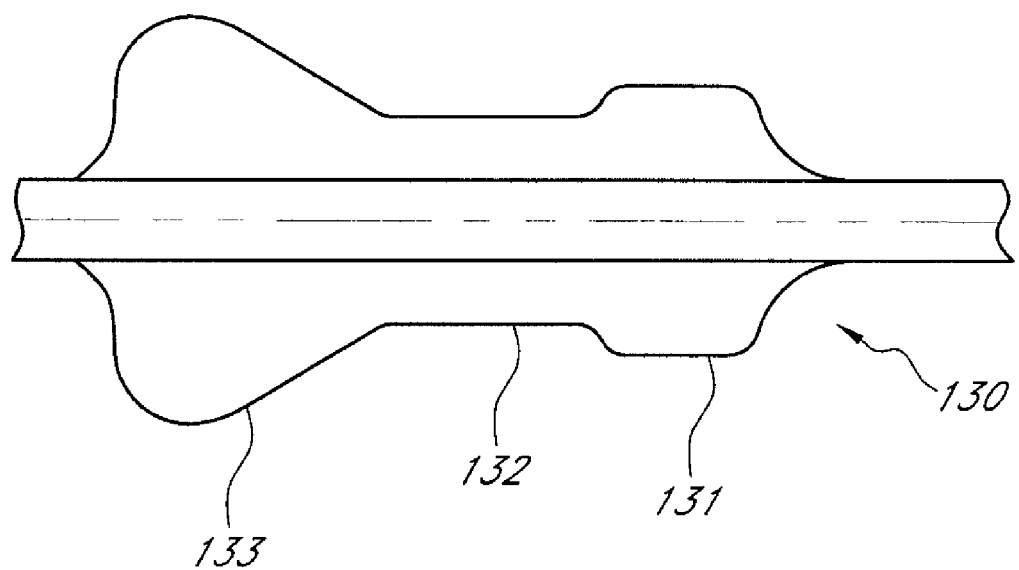
FIG. 34 is a schematic cross-sectional view of a balloon corresponding to the support structure of FIGS. 19 to 21.
Figure 35:
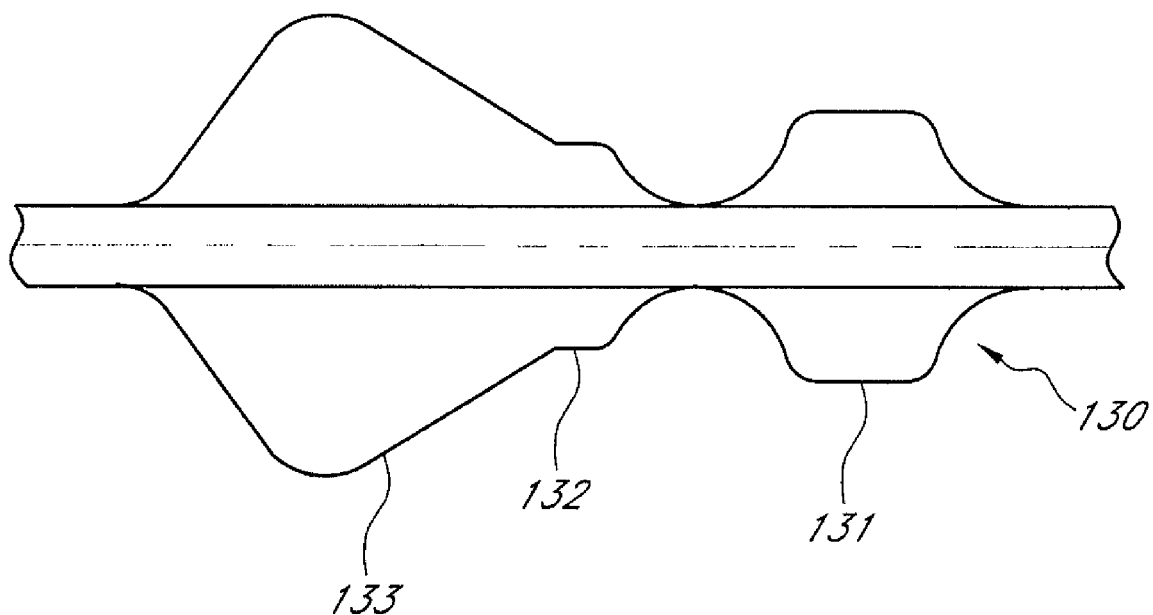
FIG. 35 is a schematic longitudinal sectional view of an alternative embodiment of the balloon of FIG. 34.

FIG. 34 shows balloon 130 making it possible to deploy support 101 according to FIGS. 19 to 21. This balloon 130 has cylindrical portion 131 whose diameter in the inflated state makes possible the expansion of holding portion 120, a cylindrical portion 132 of lesser diameter, suitable for producing the expansion of portion 103, and portion 133 in the form of a truncated cone, makes possible the expansion of portion 104. As shown by FIG. 35, portion 132 can be limited to what is strictly necessary for deploying portion 103, which makes it possible to produce balloon 130 in two parts instead of a single part, thus limiting the volume of this balloon 130.

Figure 36:
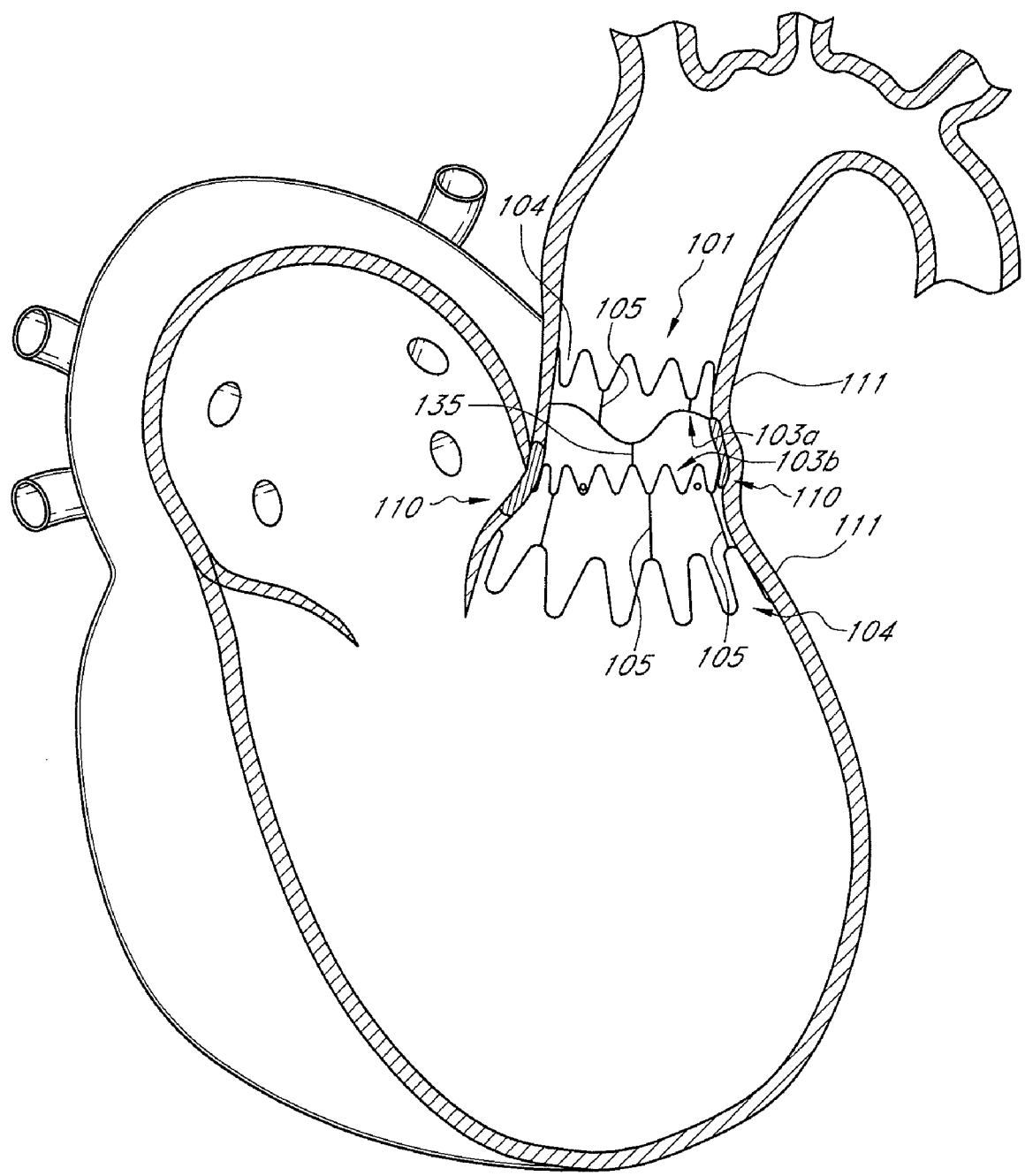
FIG. 36 is a schematic view of a heart with an embodiment of the present inventive prosthesis shown deployed in place.

FIG. 36 shows support 101 whose median portion 103 is in two parts 103a, 103b. Part 103a is made of undulating wire with large-amplitude undulations, in order to support valve 102, and part 103b, adjacent to said part 103a and connected to it by bridges 135, is made of undulating wire with small-amplitude undulations. Due to its structure, this part 103b presents a relatively high radial force of expansion and is intended to be placed opposite ring 110 in order to push back: the native valve sheets which are naturally calcified, thickened and indurated, or the residues of the valve sheets after valve resection against or into the wall of the passage. This axial portion 103a, 103b thus eliminates the problem induced by these sheets or residual sheets at the time of positioning of valve 102.

It is apparent from the preceding that one embodiment of the invention provides a tubular support for positioning, by percutaneous route, of a replacement heart valve, which provides, due to its portions 103 and 104, complete certitude as to its maintenance of position after implantation. This support also makes possible a complete sealing of the replacement valve, even in case of a cardiac ring with a surface that is to varying degrees irregular and/or calcified, and its position can be adapted and/or corrected as necessary at the time of implantation.

Figure 37:
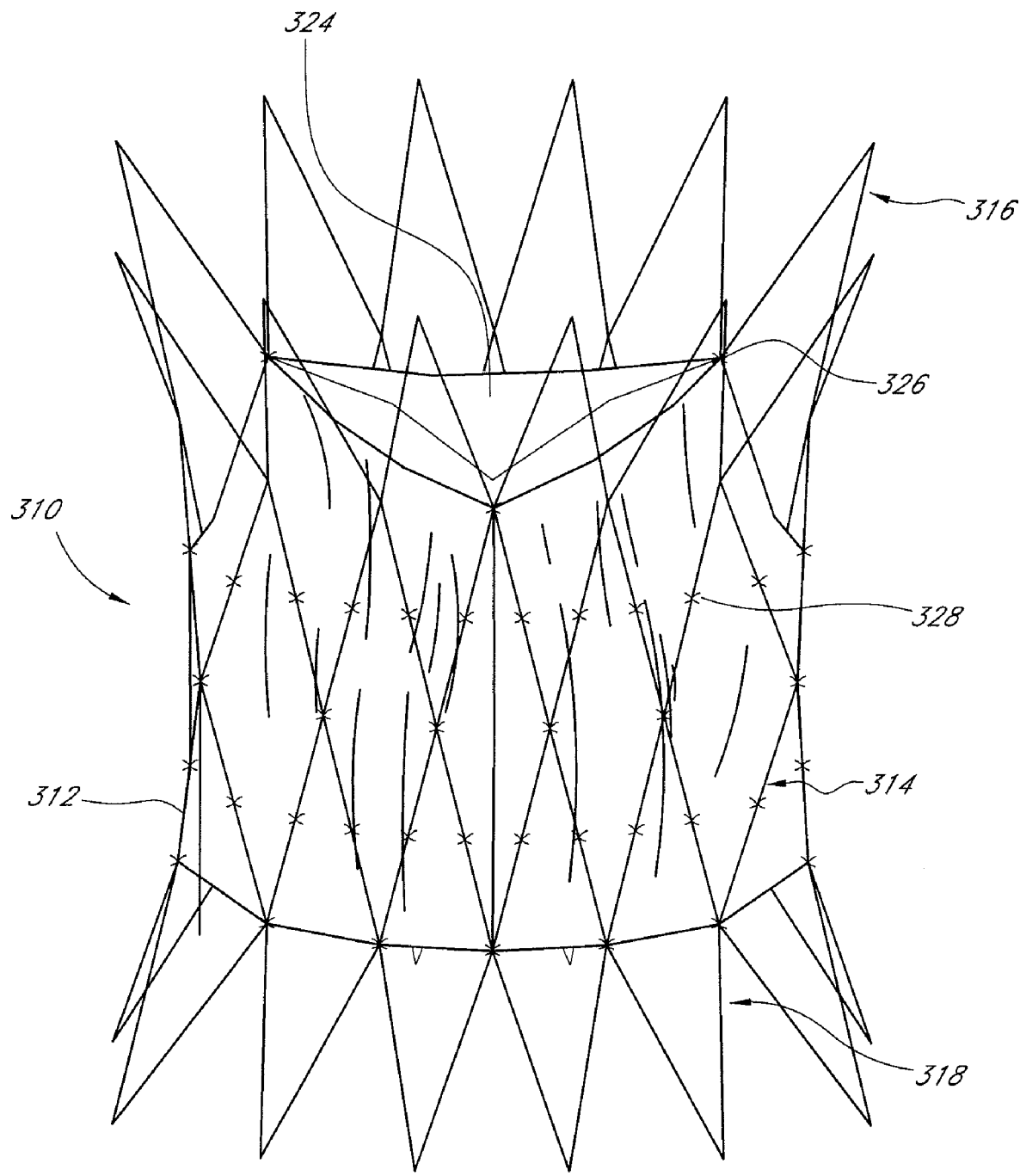
FIG. 37 is a perspective view of one embodiment of a prosthetic valve assembly of the present invention.
Figure 38:
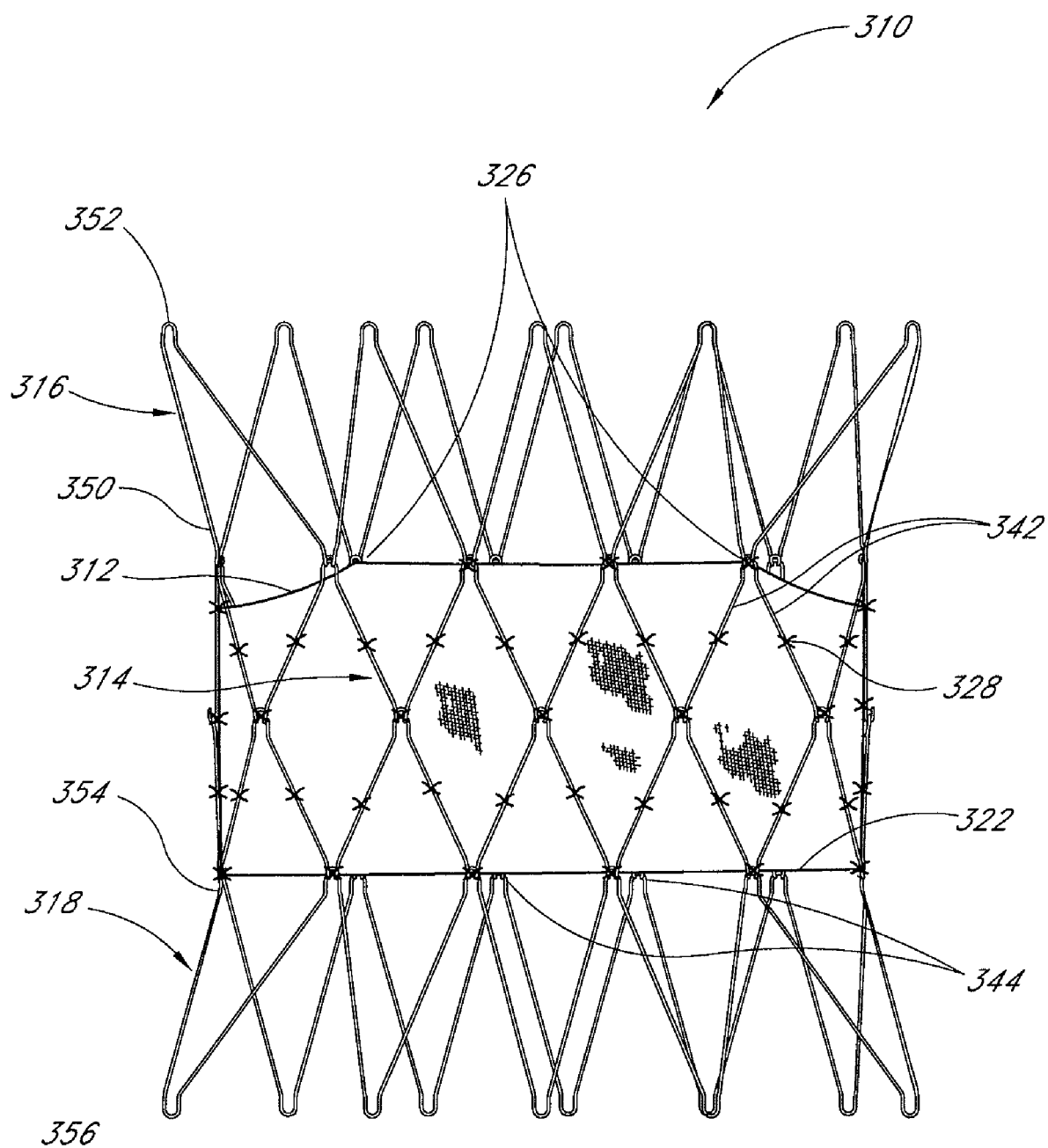
FIG. 38 is a side view of the prosthetic valve assembly of FIG. 37.

Referring to FIGS. 37 and 38, the present invention also comprises an alternative prosthetic valve assembly 310, which further comprises a prosthetic valve 312, a valve support band 314, distal anchor 316, and a proximal anchor 318. Valve 312 can be made from a biological material, such as one originating from an animal or human, or from a synthetic material, such as a polymer. Depending upon the native valve to be replaced, the prosthetic valve 312 comprises an annulus 322, a plurality of leaflets 324, and a plurality of commissure points 326. The leaflets 324 permit the flow of blood through the valve 312 in only one direction. In the preferred embodiment, the valve annulus 322 and the commissure points 326 are all entirely supported within the central support band 314. Valve 312 is attached to the valve support band 314 with a plurality of sutures 328, which can be a biologically compatible thread. The valve could also be supported on band 314 with adhesive, such as cyanoacrylate.

Figure 40:
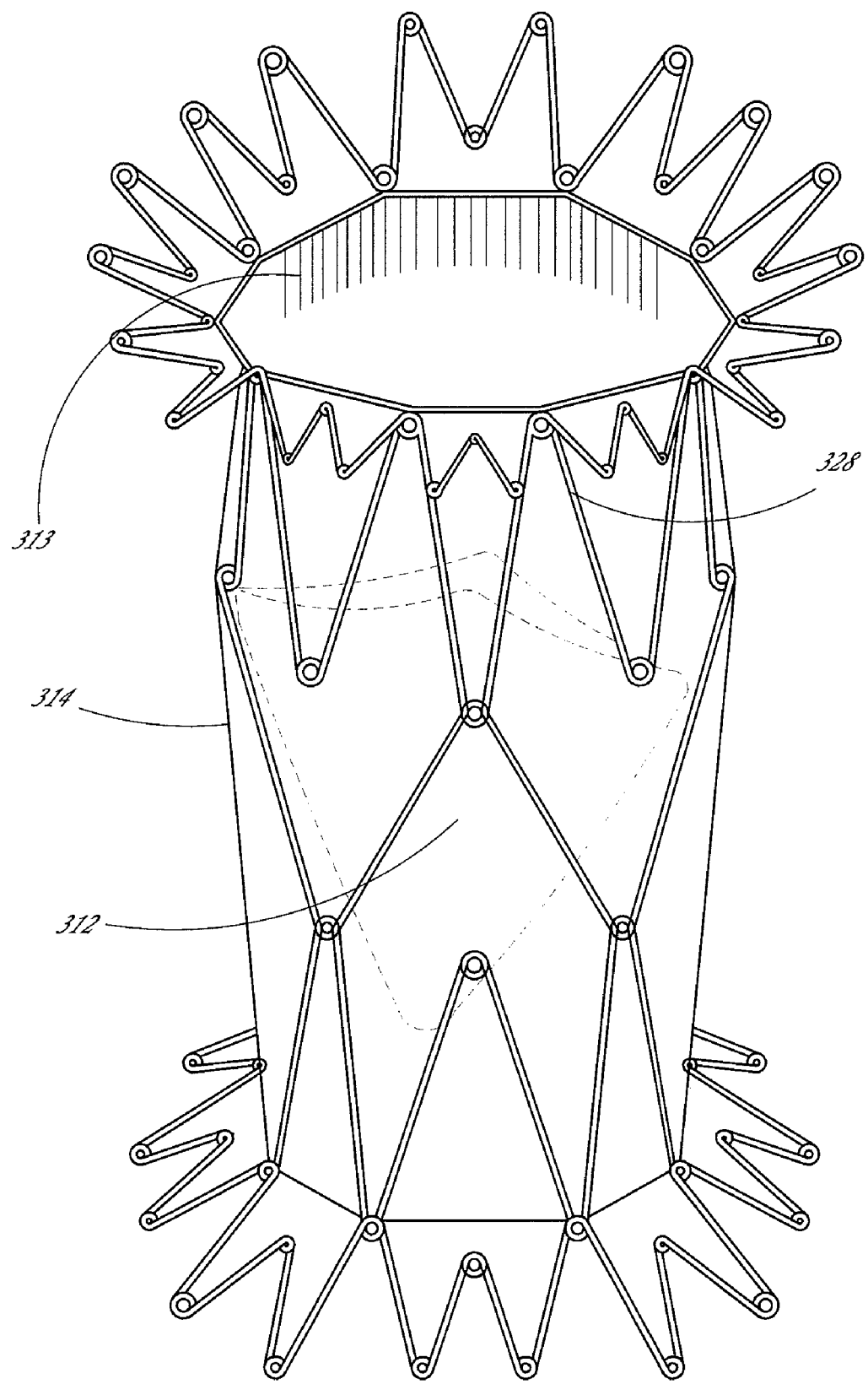
FIG. 40 is a photograph of an alternative embodiment of the prosthetic valve assembly with a sheath around the valve.

In one embodiment, valve 312 can be attached to, or may integral with, a sleeve or sheath (not shown). The sheath is secured to the valve support band 314 such that the outer surface of the sheath is substantially in contact with the inner surface of the valve support band 314. In such embodiment, the sheath can be attached to the valve support band 314 with sutures 328. FIG. 40 is a photograph of the concept of this alternative embodiment. If desired, the sheath can be secured to the outside of valve support band 314 (not shown).

Referring to FIGS. 37 and 38, in one embodiment, valve support band 314 is made from a single wire 342 configured in a zigzag manner to form a cylinder. Alternatively, valve support band 314 can be made from a plurality of wires 342 attached to one another. In either case, the band may comprise one or more tiers, each of which may comprise one or more wires arranged in a zigzag manner, for structural stability or manufacturing ease, or as anatomical constraints may dictate. If desired, even where the central valve support 314 is manufactured having more than one tier, the entire valve support 314 may comprise a single wire. Wire 342 can be made from, for example, stainless steel, silver, tantalum, gold, titanium, or any suitable plastic material. Valve support band 314 may comprise a plurality of loops 344 at opposing ends to permit attachment to valve support band 314 of anchors 316 and/or 318 with a link. Loops 344 can be formed by twisting or bending the wire 342 into a circular shape. Alternatively, valve support band 314 and loops 344 can be formed from a single wire 342 bent in a zigzag manner, and twisted or bent into a circular shape at each bend. The links can be made from, for example, stainless steel, silver, tantalum, gold, titanium, any suitable plastic material, solder, thread, or suture. The ends of wire 342 can be joined together by any suitable method, including welding, gluing or crimping.

Still referring to FIGS. 37 and 38, in one embodiment, distal anchor 316 and proximal anchor 318 each comprise a discrete expandable band made from one or more wires 342 bent in a zigzag manner similar to the central band. Distal anchor band 316 and proximal anchor band 318 may comprise a plurality of loops 344 located at an end of wire 342 so that distal anchor band 316 and proximal anchor band 318 can each be attached to valve support band 314 with a link. Loop 344 can be formed by twisting or bending the wire 342 into a circular shape. As desired, distal and/or proximal anchors 316, 318 may comprise one or more tiers, as explained before with the valve support 314. Likewise, each anchor may comprise one or more wires, regardless of the number of tiers. As explained above in regard to other embodiments, the distal anchor may be attached to the central valve support band 314 directly, as in FIG. 37, or spaced distally from the distal end of the valve support 314, as shown above schematically in FIGS. 18, 19, 21 and 22. In the later instance, one or more struts may be used to link the distal anchor band to the valve support band, as described above.

Distal anchor band 316 has a first end 350 attached to the central valve band 314, and a second end 352. Similarly, proximal anchor band 318 has first attached end 354 and a second end 356. The unattached ends 352, 356 of the anchors 316, 318, respectively are free to expand in a flared manner to conform to the local anatomy. In such embodiment the distal and proximal anchor bands 316, 318 are configured to exert sufficient radial force against the inside wall of a vessel in which it can be inserted. Applying such radial forces provides mechanical fixation of the prosthetic valve assembly 310, reducing migration of the prosthetic valve assembly 310 once deployed. It is contemplated, however, that the radial forces exerted by the valve support 314 may be sufficient to resist more than a minimal amount of migration, thus avoiding the need for any type of anchor.

In an alternative embodiment, distal and proximal anchors may comprise a fixation device, including barbs, hooks, or pins (not shown). Such devices may alternatively or in addition be placed on the valve support 314. If so desired, the prosthetic valve assembly 310 may comprise an adhesive on the exterior thereof to adhere to the internal anatomical lumen.

Figure 39:
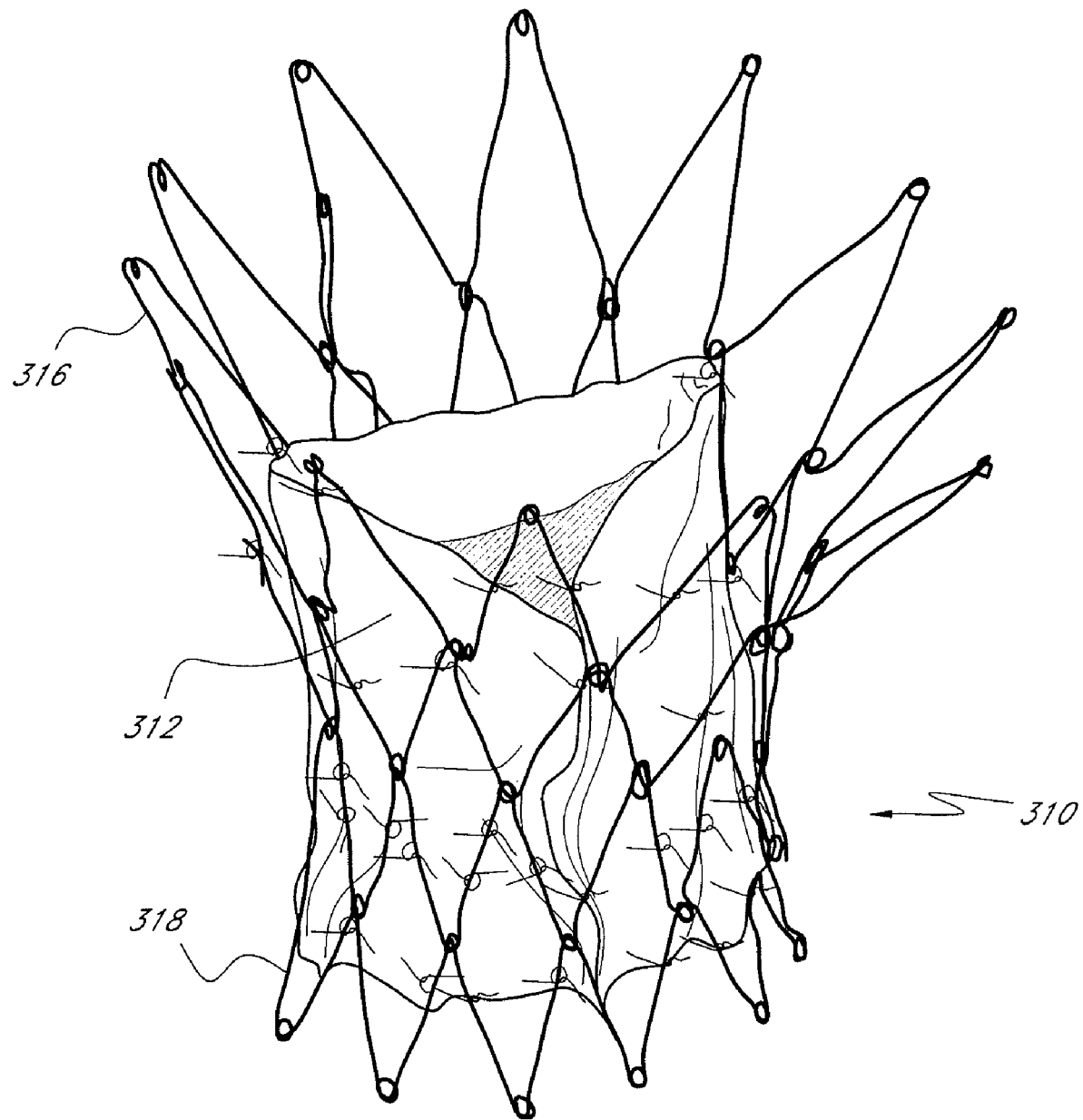
FIG. 39 is a photograph of one embodiment of the prosthetic valve assembly of FIG. 37.
Figure 49:
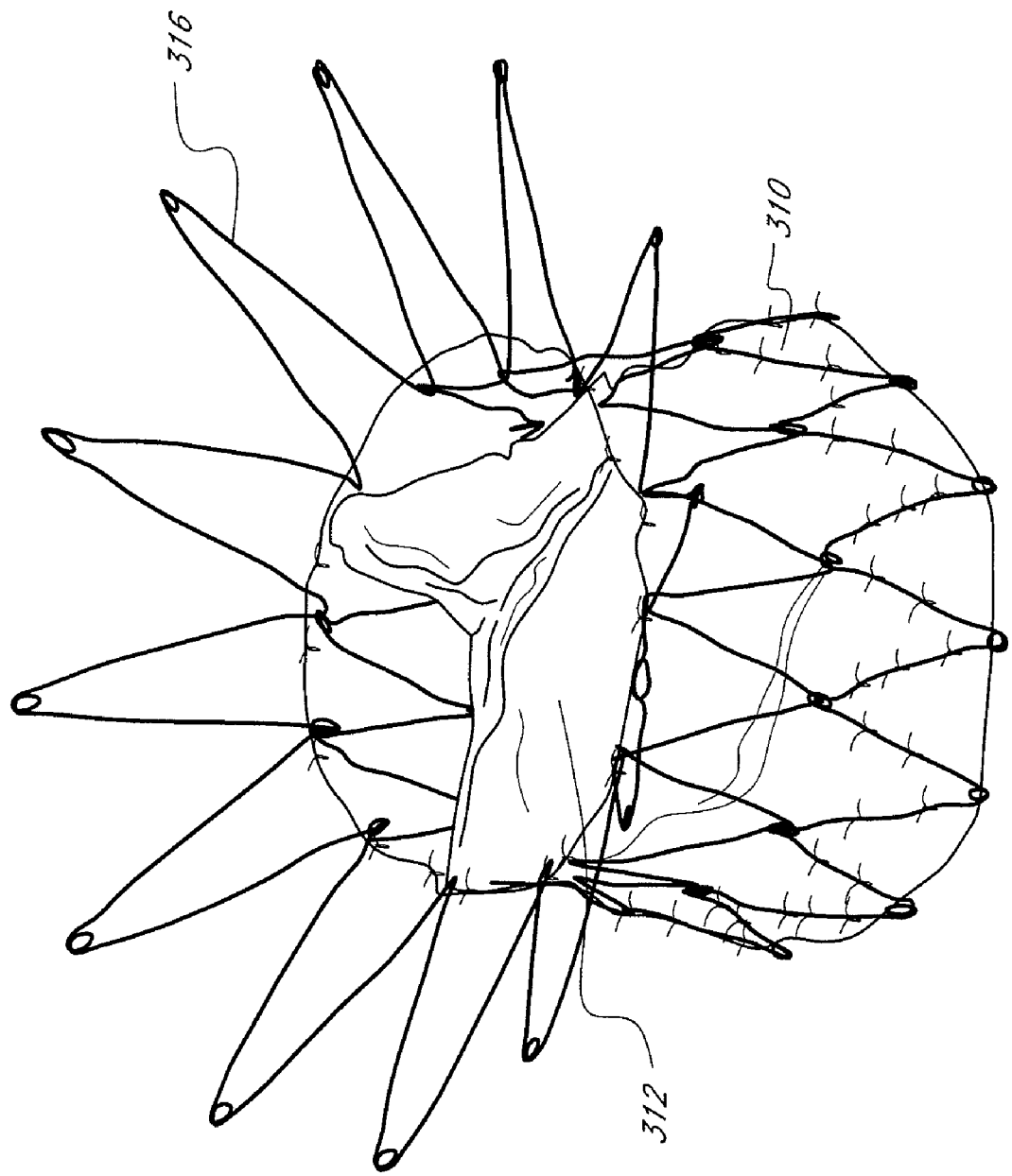
FIG. 49 is a photograph of an alternative embodiment of the prosthetic valve assembly of FIG. 37 showing only a distal anchor.

Prosthetic valve assembly 310 is compressible about its center axis such that its diameter may be decreased from an expanded position to a compressed position. When placed into the compressed position, valve assembly 310 may be loaded onto a catheter and transluminally delivered to a desired location within a body, such as a blood vessel, or a defective, native heart valve. Once properly positioned within the body the valve assembly 310 can be deployed from the compressed position to the expanded position. FIG. 39 is a photograph of one embodiment of the prosthetic valve assembly described with both distal and proximal anchor bands while FIG. 49 is a photograph showing only a distal anchor.

In the preferred embodiment, the prosthetic valve assembly 310 is made of self-expanding material, such as Nitinol. In an alternative embodiment, the valve assembly 310 requires active expansion to deploy it into place. Active expansion may be provided by an expansion device such as a balloon.

Figure 41A:
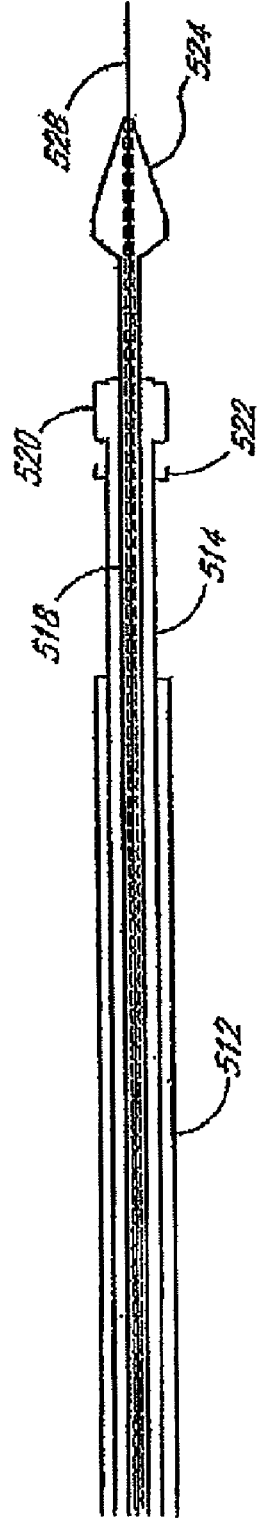
FIG. 41A is a perspective view of a distal portion of a catheter assembly for use in deploying the prosthetic valve assembly described herein.

As referred to above in association with other embodiments, the prosthetic valve assembly of the present invention is intended to be percutaneously inserted and deployed using a catheter assembly. Referring to FIG. 41A, the catheter assembly 510 comprises an outer sheath 512, an elongate pusher tube 514, and a central tube 518, each of which are concentrically aligned and permit relative movement with respect to each other. At a distal end of the pusher tube 514 is a pusher tip 520 and one or more deployment hooks 522 for retaining the prosthesis assembly (not shown). The pusher tip 520 is sufficiently large so that a contracted prosthesis assembly engages the pusher tip 520 in a frictional fit arrangement. Advancement of the pusher tube 514 (within the outer sheath 512) in a distal direction serves to advance the prosthesis relative to the outer sheath 512 for deployment purposes.

At a distal end of the central tube 518 is an atraumatic tip 524 for facilitating the advancement of the catheter assembly 510 through the patient's skin and vasculature. The central tube 518 comprises a central lumen (shown in phantom) that can accommodate a guide wire 528. In one embodiment, the central lumen is sufficiently large to accommodate a guide wire 528 that is 0.038 inch in diameter. The guide wire can slide through the total length of the catheter form tip to handle ('over the wire' catheter) or the outer sheath 512 can be conformed so as to allow for the guide wire to leave the catheter before reaching its proximal end ('rapid exchange' catheter). The space between the pusher tube 514 and the outer sheath 512 forms a space within which a prosthetic valve assembly may be mounted.

Hooks 522 on the distal end of the pusher tube 514 may be configured in any desired arrangement, depending upon the specific features of the prosthetic assembly. With regard to the prosthesis assembly of FIGS. 37 and 38, the hooks 522 preferably comprise an L-shaped arrangement to retain the prosthesis assembly axially, but not radially. With a self-expanding assembly, as the prosthesis assembly is advanced distally beyond the distal end of the outer sheath 512, the exposed portions of the prosthesis assembly expand while the hooks 522 still retain the portion of the prosthesis still housed within the outer sheath. When the entire prosthesis assembly is advanced beyond the distal end of the outer sheath, the entire prosthesis assembly is permitted to expand, releasing the assembly from the hooks. FIGS. 42 through 45 show the distal end of one embodiment of the catheter assembly, three of which show sequenced deployment of a valve prosthesis.

Figure 46:
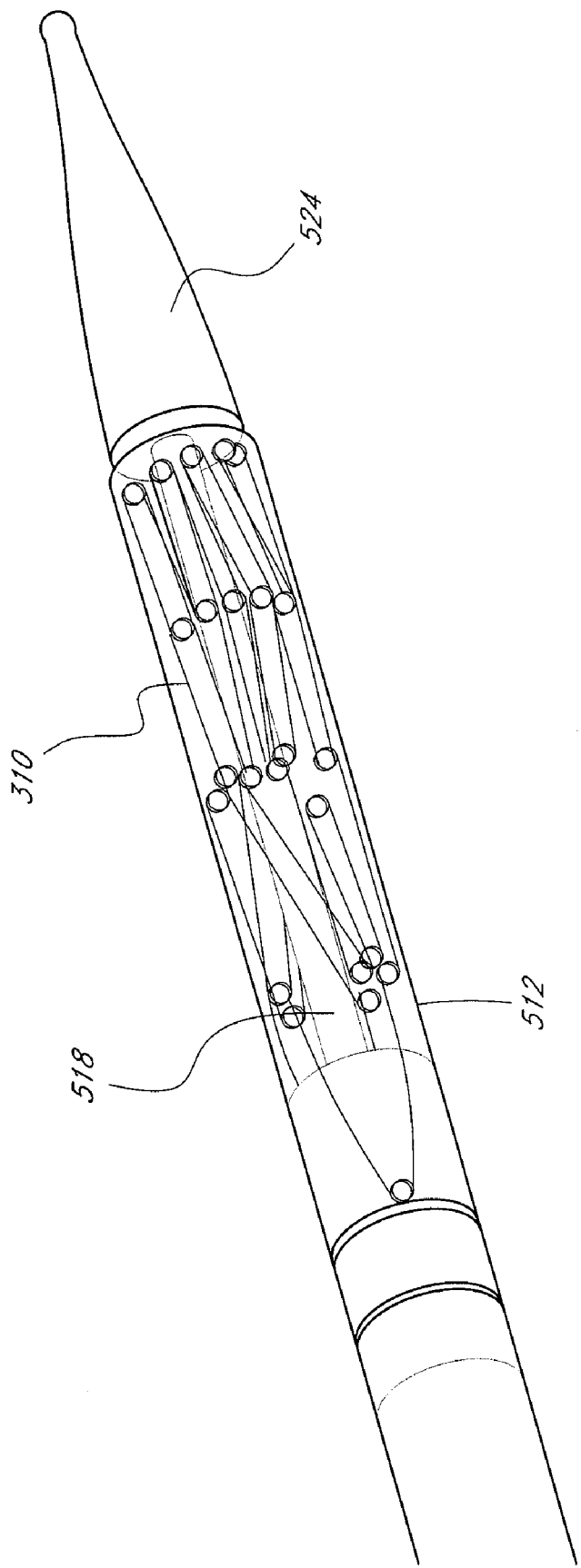
FIGS. 46 and 47 are photographs of the catheter assembly of FIG. 41A showing deployment of an alternative prosthesis assembly.
Figure 47:
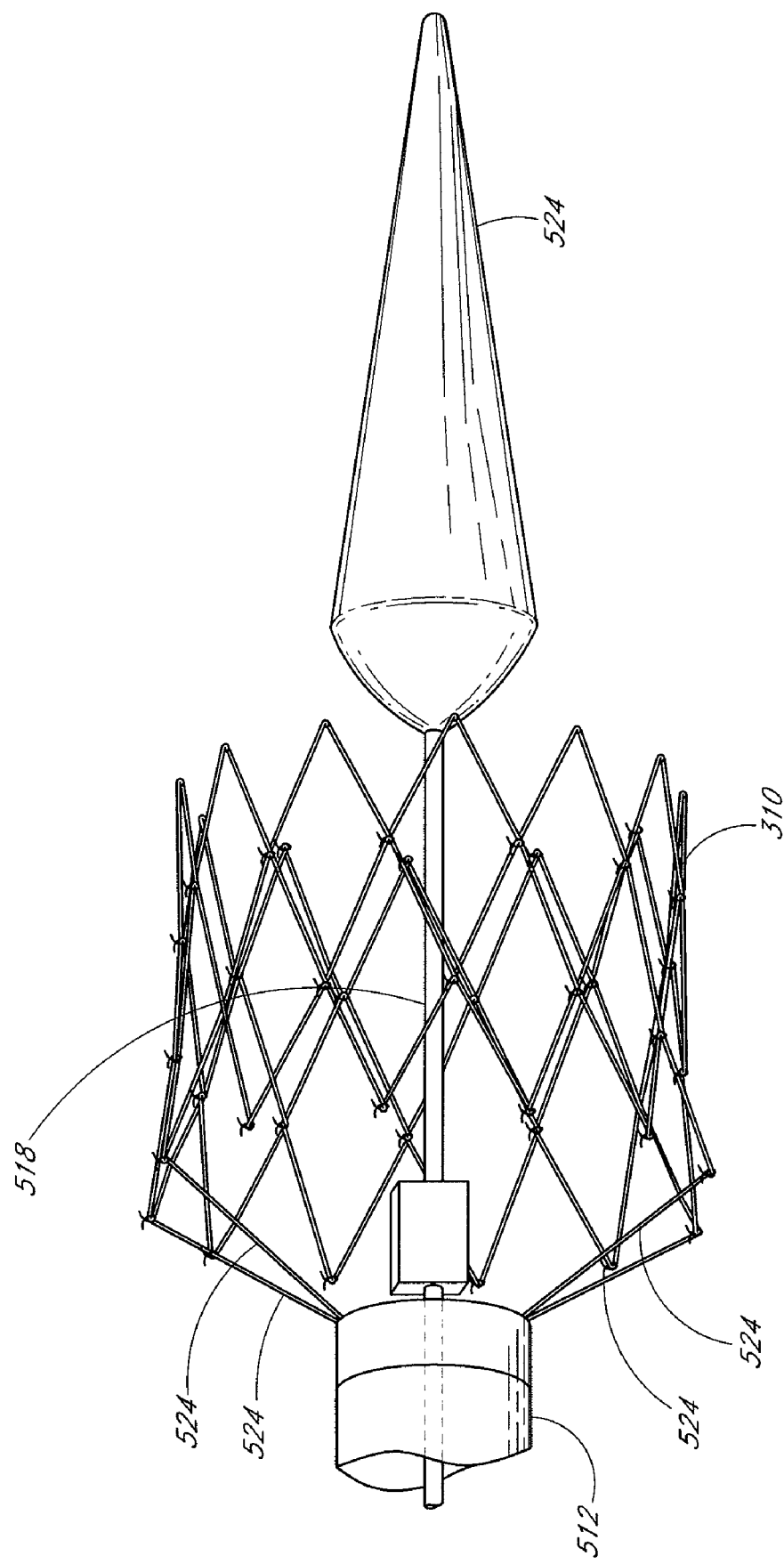
Figure 48:
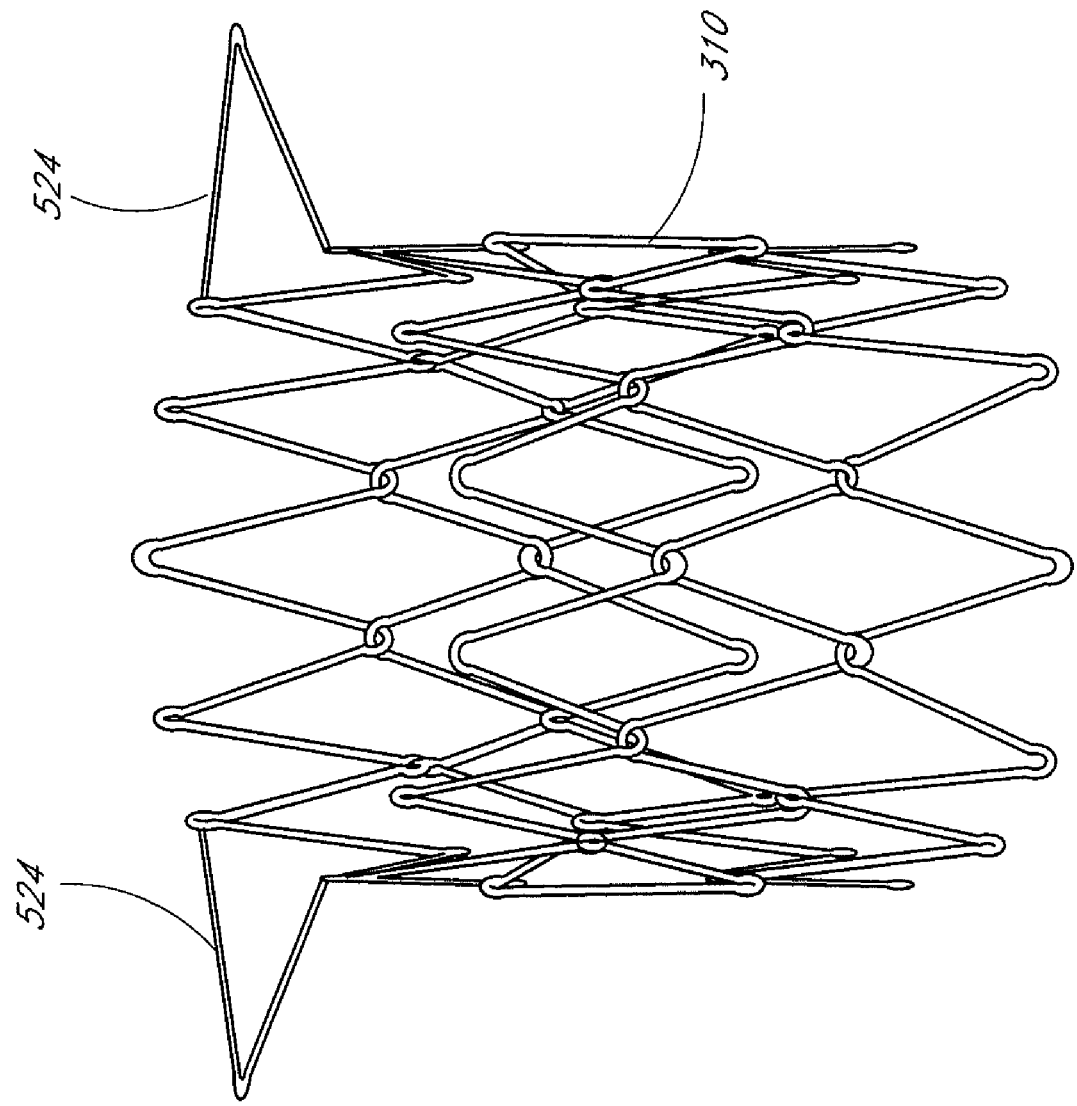
FIG. 48 is a photograph of the alternative prosthesis assembly shown in FIGS. 46 and 47.

In an alternative embodiment of the valve prosthesis, loop elements extend axially from one end of the prosthesis, where the loop elements can be retained by the hooks 522 during deployment. This alternative embodiment is shown in the photograph of FIG. 48, where the photographs of FIGS. 46 and 47 show a catheter assembly used for deploying the alternative prosthesis assembly. By adding loop elements to the prosthesis, the prosthesis may be positioned with its support and anchors fully expanded in place while permitting axial adjustment into final placement before releasing the prosthesis entirely from the catheter.

Figure 41B:
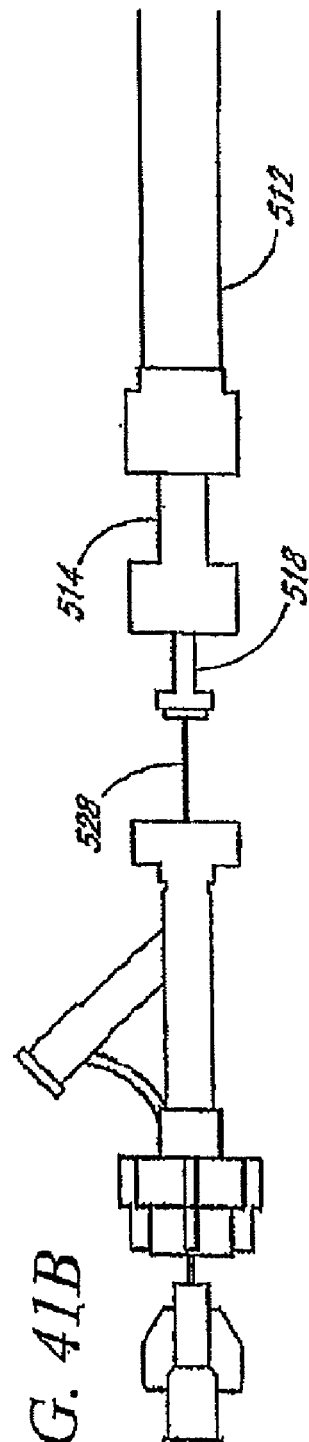
FIG. 41B is a perspective view of a proximal portion of the catheter assembly of FIG. 41A.
Figure 42:
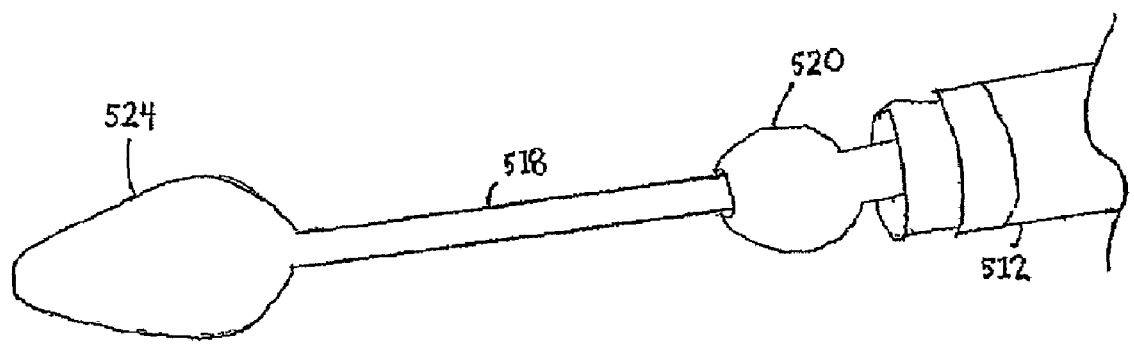
FIG. 42 is a photograph of the distal portion of the catheter assembly of FIG. 41A.
Figure 43:
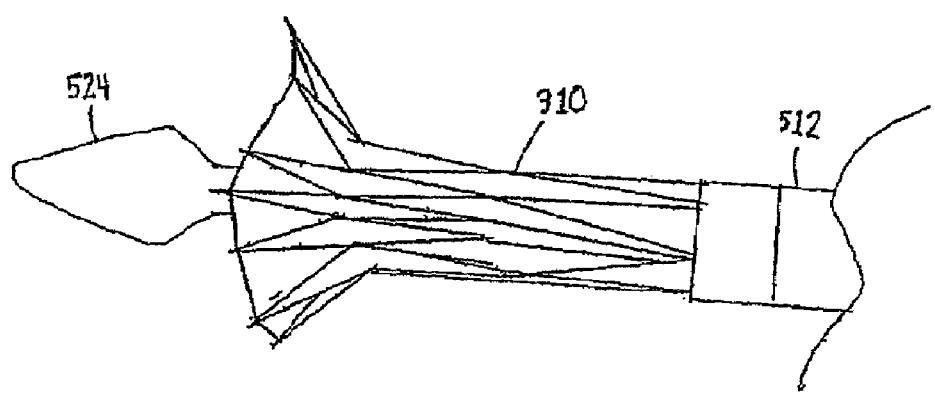
FIGS. 43 through 45 are photographs of the catheter assembly of FIG. 40A showing deployment of a prosthesis assembly in sequence.
Figure 44:
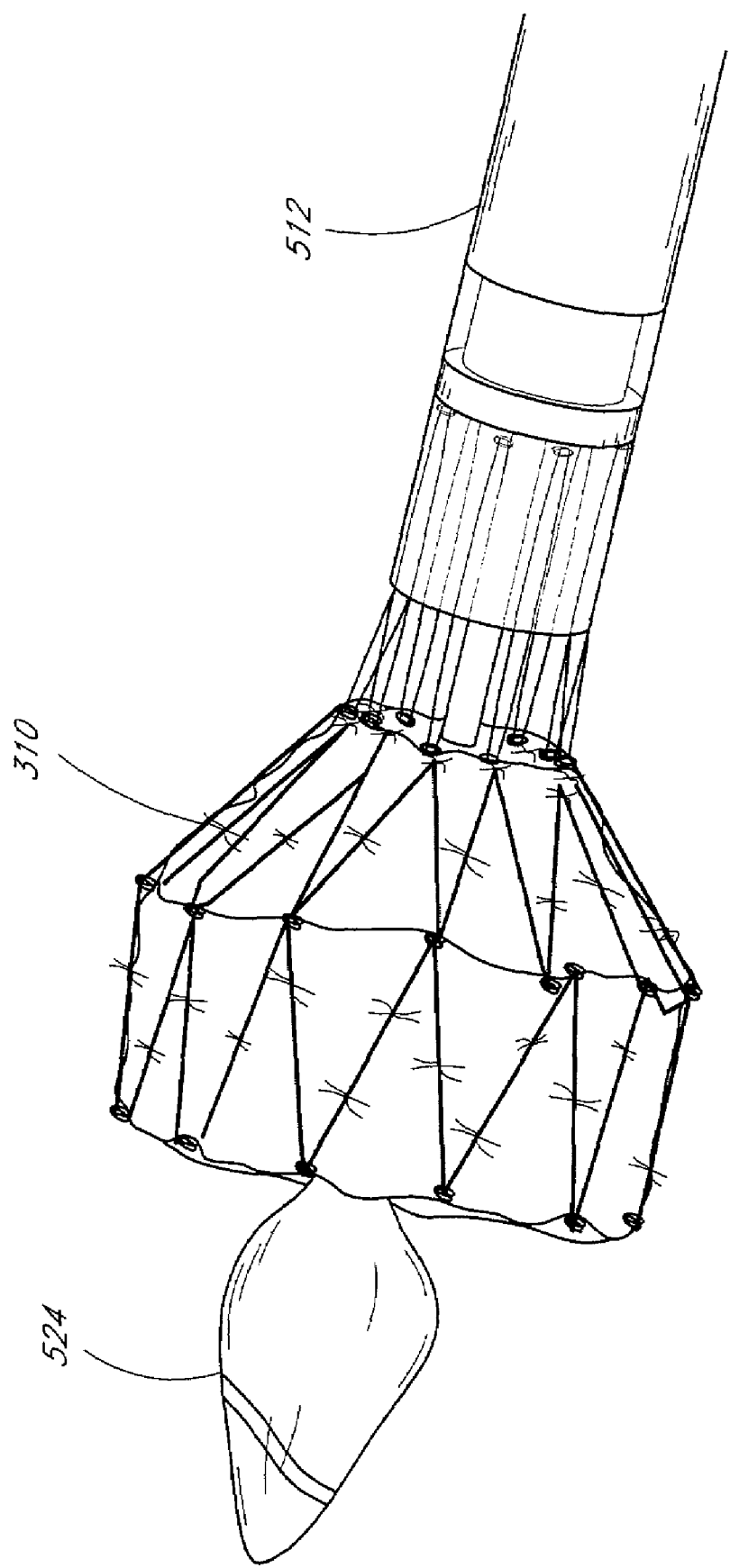
Figure 45:
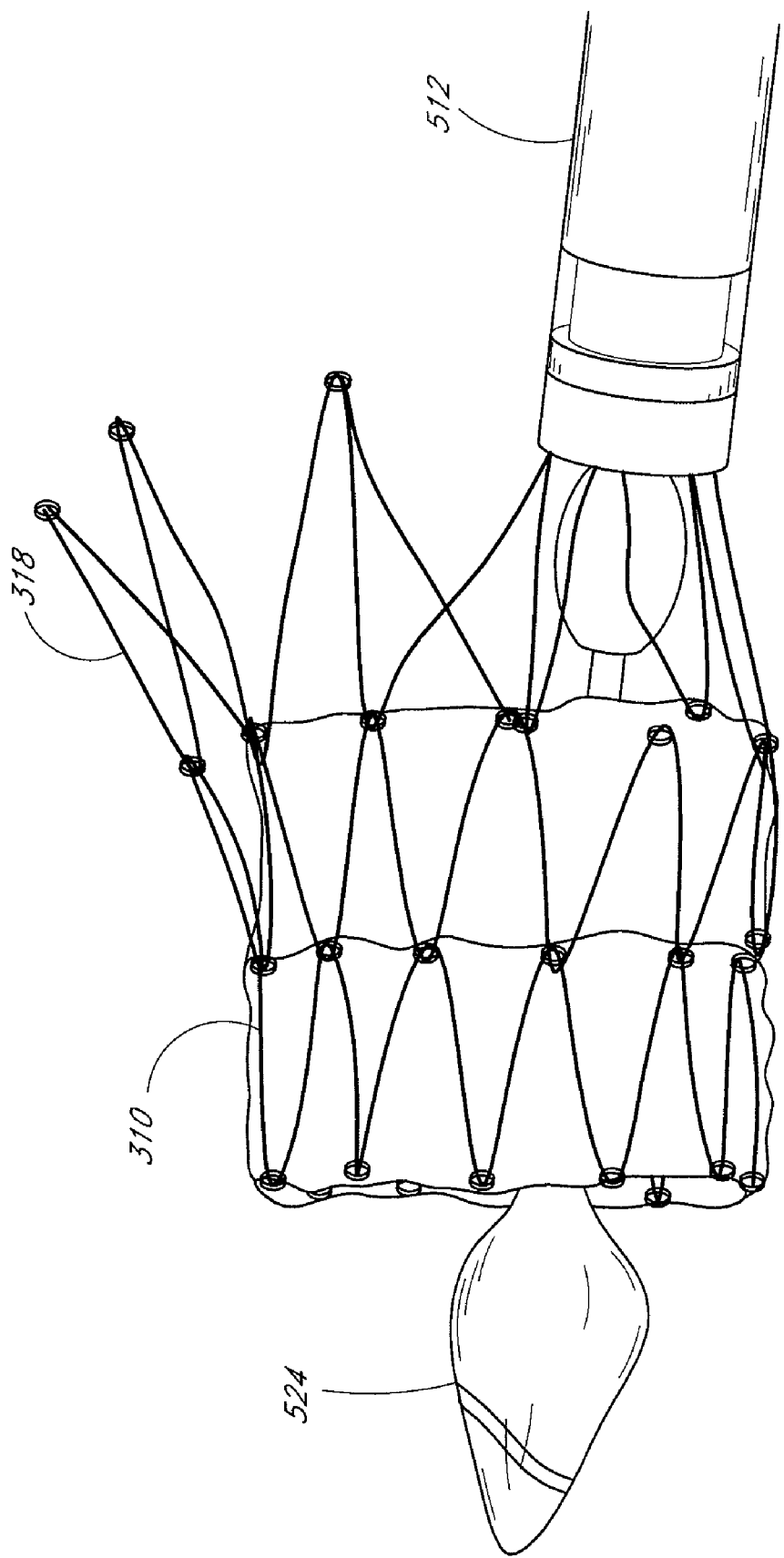

FIG. 41B shows the proximal end of the catheter assembly 510, which to a greater extent has many conventional features. At the distal end of the pusher tube 514 is a plunger 530 for advancing and retreating the pusher tube 514 as deployment of the prosthesis assembly is desired. As desired, valves and flush ports proximal and distal to the valve prosthesis may be provided to permit effective and safe utilization of the catheter assembly 510 to deploy a prosthesis assembly.

In one embodiment, prosthetic valve assembly 310 (not shown) is mounted onto catheter 510 so that the valve assembly 310 may be delivered to a desired location inside of a body. In such embodiment, prosthetic valve assembly 310 is placed around pusher tip 520 and compressed radially around the tip 520. The distal end of prosthetic valve assembly 310 is positioned on the hooks 522. While in the compressed position, outer sheath 512 is slid toward the atraumatic tip 524 until it substantially covers prosthetic valve assembly 310.

To deliver prosthetic valve assembly 310 to a desired location within the body, a guide wire 528 is inserted into a suitable lumen of the body, such as the femoral artery or vein to the right atrium, then to the left atrium through a transseptal approach, and maneuvered, utilizing conventional techniques, until the distal end of the guide wire 528 reaches the desired location. The catheter assembly 510 is inserted into the body over the guide wire 528 to the desired position. Atraumatic tip 524 facilitates advancement of the catheter assembly 510 into the body. Once the desired location is reached, the outer sheath 512 is retracted permitting the valve prosthesis to be released from within the outer sheath 512, and expand to conform to the anatomy. In this partially released state, the position of prosthetic valve 310 may be axially adjusted by moving catheter assembly 510 in the proximal or distal direction.

The present invention may be embodied in other specific forms without departing from its spirit or essential characteristics. The described embodiments are to be considered in all respects only as illustrative, and not restrictive and the scope of the invention is, therefore, indicated by the appended claims rather than by the foregoing description. All changes that come within the meaning and range of equivalency of the claims are to be embraced within their scope.

What is claimed is:

1. A prosthetic valve assembly for use in replacing a deficient native valve, the valve assembly comprising:
    a valve having a plurality of leaflets, a base, and a plurality of commissure points;
    a valve support comprising a generally cylindrical band comprising a plurality of expandable cells, the valve support configured to be collapsible for transluminal delivery and expandable to contact the anatomical annulus of the native valve when the assembly is positioned in situ, said generally cylindrical band of the valve support supporting the base and the commissure points of the valve; and
    an anchor for engaging the lumen wall when expanded in place for preventing substantial migration of the valve assembly after deployment:
    wherein the anchor comprises one or more hooks extending radially outward from the valve support.

2. The valve assembly of claim 1, wherein the valve support comprises nickel titanium.

3. A method of replacing a deficient native valve comprising the steps of:
    providing a prosthetic valve assembly, the assembly comprising a valve, a valve support comprising a plurality of expandable cells and having the base and the commissures of the valve positioned and secured at or adjacent the expandable cells, the valve support further comprising an anchor;
    collapsing the valve support and anchor to fit on a distal portion of a catheter;
    advancing the catheter to the deficient native valve to a position within adjacent the leaflets and within the annulus of the deficient native valve;
    deploying the valve assembly within the deficient native valve, whereby the valve support expands against the leaflets of the deficient native valve; and
    withdrawing the catheter, leaving the valve assembly to function in place of the deficient native valve.

4. The method of claim 3, further comprising the step of positioning the valve support and anchor within a generally tubular sheath extending around the distal portion of the catheter.

5. The method of claim 3, wherein the anchor is self-expanding.

6. The method of claim 3, wherein the valve support is self-expanding.

7. The method of claim 3, wherein the valve support is balloon-expandable.

8. The method of claim 3, further comprising the step of securing a portion of the valve support to the catheter.

9. The method of claim 3, wherein deploying the valve assembly comprises the step of crushing the native valve leaflets against the native valve annulus.

10. The method of claim 3, wherein the prosthetic valve assembly further comprises an anchor for engaging a lumen wall for preventing substantial migration of the valve assembly when positioned in place.

11. The method of claim 10, wherein the anchor is spaced from the valve support.

12. A prosthetic valve assembly for use in replacing a deficient native valve, the valve assembly comprising:
    a valve having a base, a plurality of leaflets and commissure points;
    a valve support comprising a plurality of expandable cells and a plurality of longitudinal bars, the valve support configured to be collapsible for transluminal delivery and expandable to contact the anatomical annulus of the native valve when the assembly is positioned in situ, said valve support supporting the base, wherein the commissure points of the valve are secured at the longitudinal bars and adjacent one or more of the expandable cells, and wherein the longitudinal bars of the valve support further comprise a plurality of holes, wherein the plurality of leaflets are secured to the longitudinal bars via suture lines passing through the plurality of holes.

13. The valve assembly of claim 12, wherein the valve support is self-expanding.

14. The valve assembly of claim 12, wherein the valve support is balloon expandable.

15. The valve assembly of claim 12, wherein the valve support is configured to press radially against the native valve leaflets to hold the native valve leaflets against walls of the native valve annulus and/or against walls of an adjacent lumen to thereby prevent the native valve leaflets from obstructing the native valve annulus.

* * * * *

(12) INTER PARTES REEXAMINATION CERTIFICATE (1068th)
United States Patent
Seguin et al.

(10) Number: US 7,892,281 C1
(45) Certificate Issued: *Mar. 13, 2015

(54) PROSTHETIC VALVE FOR TRANSLUMINAL DELIVERY

(75) Inventors: Jacques Seguin, Old Windsor (GB); Georg Börtlein, Meudon (FR)

(73) Assignee: Medtronic CoreValve LLC, Minneapolis, MN (US)

Reexamination Request:
No. 95/001,921, Mar. 2, 2012

Reexamination Certificate for:
Patent No.: 7,892,281
Issued: Feb. 22, 2011
Appl. No.: 12/348,892
Filed: Jan. 5, 2009

( * ) Notice: This patent is subject to a terminal disclaimer.

Related U.S. Application Data

(63) Continuation of application No. 12/029,031, filed on Feb. 11, 2008, which is a continuation of application (Continued)

(30) Foreign Application Priority Data

Nov. 17, 1999 (FR) ..................................... 99 14462

(51) Int. Cl.
*A61F 2/24* (2006.01)
*A61B 17/02* (2006.01)

(52) U.S. Cl.
CPC ........... *A61F 2/2433* (2013.01); *A61B 17/0218* (2013.01); *A61F 2/2412* (2013.01); *A61F 2/2418* (2013.01); *A61F 2/2436* (2013.01); *A61F 2210/0023* (2013.01); *A61F 2250/0003* (2013.01); *A61F 2250/0039* (2013.01); *A61F 2250/0048* (2013.01); *A61F 2250/0069* (2013.01); *Y10S 623/904* (2013.01); *A61F 2220/0008* (2013.01); *A61F 2220/0016* (2013.01); *A61F 2220/005* (2013.01); *A61F 2220/0075* (2013.01); *A61F 2230/005* (2013.01); *A61F 2230/0054* (2013.01); *A61F 2230/0067* (2013.01)
USPC ........................................... 623/2.1; 623/904

(58) Field of Classification Search
None
See application file for complete search history.

(56) References Cited

To view the complete listing of prior art documents cited during the proceeding for Reexamination Control Number 95/001,921, please refer to the USPTO's public Patent Application Information Retrieval (PAIR) system under the Display References tab.

*Primary Examiner* — Jimmy G Foster

(57) ABSTRACT

A prosthetic valve assembly for use in replacing a deficient native valve comprises a replacement valve supported on an expandable valve support. If desired, one or more anchor may be used. The valve support, which entirely supports the valve annulus, valve leaflets, and valve commissure points, is configured to be collapsible for transluminal delivery and expandable to contact the anatomical annulus of the native valve when the assembly is properly positioned. The anchor engages the lumen wall when expanded and prevents substantial migration of the valve assembly when positioned in place. The prosthetic valve assembly is compressible about a catheter, and restrained from expanding by an outer sheath. The catheter may be inserted inside a lumen within the body, such as the femoral artery, and delivered to a desired location, such as the heart. When the outer sheath is retracted, the prosthetic valve assembly expands to an expanded position such that the valve and valve support expand within the deficient native valve, and the anchor engages the lumen wall.

Attention is directed to the decision of *Medtronic Corevalve LLC et al v. Edwards Lifesciences LLC et al.*, Fed. Cir., 2013-1117, upheld finding of invalidity of claims 3, 4, 7, 12, 14 and 15 by US Dist. Ct. Central California, regarding same parties in 8:11cv961 relating to this patent. This reexamination may not have resolved all questions raised by this decision. See 37 CFR 1.552(c) for *ex parte* reexamination and 37 CFR 1.906(c) for *inter partes* reexamination.

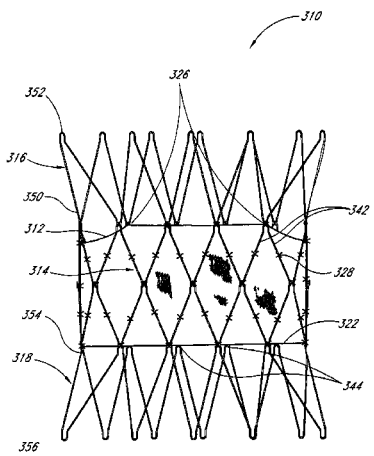

Related U.S. Application Data

No. 11/352,614, filed on Feb. 13, 2006, now Pat. No. 7,329,278, which is a continuation of application No. 10/412,634, filed on Apr. 10, 2003, now Pat. No. 7,018,406, which is a continuation-in-part of application No. 10/130,355, filed as application No. PCT/FR00/03176 on Nov. 15, 2000, now Pat. No. 6,830,584, and a continuation-in-part of application No. PCT/FR01/03258, filed on Oct. 19, 2001, said application No. 12/348,892 is a continuation of application No. 11/434,506, filed on May 15, 2006, which is a continuation-in-part of application No. 10/772,101, filed on Feb. 4, 2004, which is a continuation-in-part of application No. 10/412,634.

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-15 are cancelled.

\* \* \* \* \*